(12) United States Patent
Chen et al.

(10) Patent No.: US 11,149,060 B2
(45) Date of Patent: Oct. 19, 2021

(54) FUNCTIONALIZED NANOPARTICLES FOR ENHANCED AFFINITY PRECIPITATION OF PROTEINS

(71) Applicants: Wilfred Chen, Hockessin, DE (US); Andrew Swartz, Newark, DE (US)

(72) Inventors: Wilfred Chen, Hockessin, DE (US); Andrew Swartz, Newark, DE (US)

(73) Assignee: University of Delaware, Newark, DE (US)

(*) Notice: Subject to any disclaimer, the term of this patent is extended or adjusted under 35 U.S.C. 154(b) by 100 days.

(21) Appl. No.: 16/076,418

(22) PCT Filed: Feb. 17, 2017

(86) PCT No.: PCT/US2017/018505
§ 371 (c)(1),
(2) Date: Aug. 8, 2018

(87) PCT Pub. No.: WO2017/143286
PCT Pub. Date: Aug. 24, 2017

(65) Prior Publication Data
US 2019/0048039 A1    Feb. 14, 2019

Related U.S. Application Data

(60) Provisional application No. 62/297,173, filed on Feb. 19, 2016.

(51) Int. Cl.
| | |
|---|---|
| *C07K 1/32* | (2006.01) |
| *C07K 1/22* | (2006.01) |
| *B82Y 5/00* | (2011.01) |
| *C07K 14/78* | (2006.01) |
| *C12N 9/02* | (2006.01) |
| *C12N 9/64* | (2006.01) |

(52) U.S. Cl.
CPC .............. *C07K 1/32* (2013.01); *B82Y 5/00* (2013.01); *C07K 1/22* (2013.01); *C07K 14/78* (2013.01); *C12N 9/0008* (2013.01); *C12N 9/6472* (2013.01); *C07K 2319/00* (2013.01); *C07K 2319/01* (2013.01); *C07K 2319/70* (2013.01); *C12Y 101/01081* (2013.01); *C12Y 304/2207* (2013.01)

(58) Field of Classification Search
None
See application file for complete search history.

(56) References Cited

U.S. PATENT DOCUMENTS

| 5,641,515 A | 6/1997 | Ramtoola |
| 2002/0164372 A1 | 11/2002 | Pestka |
| 2008/0044438 A1 | 2/2008 | Ostroff et al. |
| 2016/0002289 A1 | 1/2016 | Kokke et al. |
| 2016/0018406 A1 | 1/2016 | Freire et al. |

OTHER PUBLICATIONS

Arnau et al. Protein Expression and Purification, vol. 48, pp. 1-13, 2006.*
Beck et al., Nat Rev Immunol., 10:345-52 (2010).
Boulet-Audet et al., Anal. Chem., 86:9786-93 (2014).
Brownlee et al., J. Immunol. Methods, 407:120-26 (2014).
Chen et al., Chem. Comm., 51:12107-10 (2015).
Chilkoti et al., Curr Opin Chem Biol., 10(6):652-57 (2006).
Domingo et al., J. Mol. Biel., 305(2):259-67 (2001).
Ecker et al., mAbs 7(1):9-14 (2015).
Ghose et al., Biotechnol Bioeng., 92(6):665-73 (2005).
Ghose et al., Biotechnol. Bioeng., 96(4):768-79 (2007).
Hilbrig and Freitag, Journal Chromatography B, 790:79-90 (2003).
Ho et al., Chem. Commun., 51:2107-10 (2015).
Huang et al., Biotechnol. Prog., 26(5):1400-10 (2010).
International Preliminary Report on Patentability for International Application No. PCT/US2017/018505, dated Aug. 21, 2018, 15 pages.
International Search Report and Written Opinion for International Application No. PCT/US2017/018505, dated May 2017, 17 pages.
Jendeberg et al., Journal Molecular Recognition, 8:270-78 (1995).
Kim et al., Anal. Chem., 77:2318-22 (2005).
Levary et al., PLoS ONE, 6(1):e18342, pp. 1-6 (2011).
Lim et al., Biomacromolecules, 8:1417-24 (2007).
Löfdahl et al., Proc. Natl. Acad, Sci., 80:697-701 (1983).
Madan et al., Journal Biotechnology, 163:10-16 (2013).
McPherson et al., Protein Expression and Purification. 7:51-57 (1996).
Meyer and Chilkoti, Nature Biotechnology, 17:1112-15 (1999).
Meyer et al., Biotechnol. Prog., 17:720-28 (2001).
Nettles et al., Adv Drug Deliv Rev., 62(15):1479-85 (2010).
Savitski et al., Science, 346(6205):1-10 (2014).
Sheth et al., Biotechnol. Bioeng., 110(10):2664-76 (2013).
Sheth et al., Biotechnol. Bioeng., 111(8):1595-603 (2014).
Shukla and Thömmes, Trends Biotechnol., 28(5):253-61 (2010).
Sun et al., ACS Nano, 9(8):8554-61 (2015).
Taipa et al., Bioseparation, 9:291-98 (2001).
Takei et al., Bioconjugate Chem., 5:577-82 (1994).
Tanaka et al., ChemBioChem, 9:802-7 (2008).
Thömmes and Etzel, Biotechol. Prog., 23:42-45 (2007).
Urry, J. Phys. Chem. B, 101:11007-28 (1997).
Zhou et al., The Journal of Biological Chemistry, 276(24):21704-13 (2001).
Zhou et al., PNAS, 98(26):14802-07 (2001).

(Continued)

*Primary Examiner* — Yunsoo Kim
(74) *Attorney, Agent, or Firm* — RatnerPrestia

(57) ABSTRACT

The present invention provides a nanoparticle capable of binding specifically to a target protein in a solution and precipitating with the target protein out of the solution upon addition of the target protein to the solution. The precipitation may be reversed release the target protein from the nanoparticle, which may be reused for precipitating the target protein. Also provided are a method for purifying a target protein by affinity precipitation using the nanoparticle without chromatography and a method for preparing the nanoparticle.

17 Claims, 9 Drawing Sheets

Specification includes a Sequence Listing.

(56) References Cited

OTHER PUBLICATIONS

Kirchhofer, A., et al. "Modulation of protein properties in living cells using nanabodies," Nature Structural & Molecular Biology, 17(1), Jan. 2010: 133-139.

Swartz, A.R., et al. "High-efficiency affinity precipitation of multiple industrial mAbs and Fc-fusion proteins from cell culture harvests using Z-ELP-E2 nanocages," Biotechnology and Bioengineering 115.8, (2018): 2039-2047.

Swartz, A.R., et al, "SpyTag/SpyCatcher functionalization of E2 nanocages with stimuli-responsive Z-ELP affinity domains for tunable monoclonal antibody binding and precipitation properties," Bioconjugate Chemistry. 29, (2018): pp. 3113-3120.

Tang, J.C.Y., et al., "A nanobody-based system using fluorescent proteins as scaffolds for cell-specific gene manipulation," Cell, 154, (2013): pp. 928-939.

\* cited by examiner

FUNCTIONALIZED NANOPARTICLES FOR ENHANCED AFFINITY PRECIPITATION OF PROTEINS

CROSS-REFERENCE TO RELATED APPLICATION

This application is a U.S. national phase application of International Application No. PCT/US2017/018505, filed Feb. 17, 2017 claiming the benefit of U.S. Provisional Application No. 62/297,173, filed Feb. 19, 2016, the contents of which are incorporated herein by reference in their entireties for all purposes.

REFERENCE TO U.S. GOVERNMENT SUPPORT

This work is supported by a grant from the National Science Foundation Grant No. CBET1403697. The United States has certain rights in the invention.

FIELD OF THE INVENTION

The invention relates generally to nanoparticles for enhancing affinity precipitation of target proteins, especially antibodies.

BACKGROUND OF THE INVENTION

Monoclonal antibodies represent a rapidly expanding class of biopharmaceutical therapeutics that target a wide range of diseases. To meet the increasing demand, recent advancements in upstream culture productivity and scale-up have yielded significantly higher antibody titers within bioreactors as large as 20,000 L. This has placed a significant burden on the downstream purification platform, especially the primary capture step, Protein A affinity chromatography. The protein A ligand, derived from a gene in *Staphylococcus aureus*, binds to the $F_c$ region of human immunoglobulin G (IgG) and can be recombinantly expressed in *Escherichia coli*. Protein A chromatography has been widely recognized as the gold standard in platform mAb purification due to its high selectivity and yield. However, current limitations on throughput, scale-up, and cost have generated increased interest in non-chromatographic alternative technologies.

Protein precipitation is one purification technique that is commonly used for its cost efficiency and simple scale up, but it lacks in selectivity. Affinity precipitation is an ideal alternative, because it combines the high selectivity of an affinity ligand, such as Protein A, with the operational benefits of precipitation. An example affinity precipitation of a target protein requires binding to a ligand, an environmental stimulus to precipitate the complex, a separation of insoluble and soluble solution components, and a second stimulus to elute the target protein from the ligand. In conventional affinity precipitation processes, the first stimulus requires a solution with salt concentrations exceeding 1 M at temperatures as high as 37° C. The second stimulus required for elution may require a pH less than 4 at low salt concentrations and temperatures.

Thermally responsive synthetic polymers have been implemented for IgG affinity precipitation, such as Eudragit S-100 and Poly(N-isopropylacrylamide), but the production of these polymers require rigorous and expensive chemical synthesis steps. Alternatively, elastin-like polypeptides (ELPs) are thermally responsive biopolymers composed of a pentameric amino acid repeat sequence of Val-Pro-Gly-X-Gly (SEQ ID NO: 1), where X is a guest residue that can be any amino acid except proline. The reversible phase transition properties of ELPs are dependent on the ionic strength and/or temperature of the solution relative to a critical point called the transition temperature ($T_t$). As the solution approaches the transition, a conformational change occurs, exposing the ELP's internal hydrophobic residues, leading to the formation of insoluble aggregates that can be separated from other soluble impurities through centrifugation or filtration. This process is typically reversible, such that the salt can be diluted out and/or the temperature can be lowered below the $T_t$, allowing the ELP to re-solubilize back into solution. This ELP precipitation and resolubilization process was termed inverse transition cycling (ITC) and can be repeated numerous times.

An ELP-fusion with a small (7 kDa) synthetic domain called the Z-domain derived from the B domain in Protein A binds to IgG with high affinity and has the capability to precipitate and elute antibodies. One major limitation of using Z-ELP in antibody purification is the requirement of high temperatures, as high as 37° C., and high salt concentrations, as high as 1.5 M, for precipitation. These conditions are necessary to form large enough aggregates for efficient pelleting by centrifugation or retention by filtration. However, exposure to elevated temperature and/or salt has been shown to result in antibody aggregation, denaturation, and loss of activity. Moreover, the requirement of a heating step for precipitation and a cooling step for elution presents an additional operational burden, especially at large scale. Lastly, excess heat or salt may cause non-specific precipitation of unwanted impurities and a decrease in purification efficiency.

There remains a need for improvement upon the shortcomings of existing affinity precipitation technologies for protein purification by, for example, minimizing salt and/or temperature required for the precipitation, thereby improving product quality and purification. An affinity precipitation capturing scaffold that is capable of isothermal phase transition with low salt concentrations is highly desirable.

One way to improve affinity precipitation without increasing salt or temperature is to enlarge the dimension of the capturing scaffold. Protein nanoparticles are ideal scaffolds because they assemble from small building blocks into large, 10-100 nm structures, and allow for multisite functionalization of their exterior surface using common conjugation techniques. In addition, the localization of affinity ligands on nanoparticles may lead to cross linking through multi-valent binding to a target protein. One example of a protein nanoparticle is the E2 core of the pyruvate dehydrogenase enzyme complex from *Bacillus stearothermophilus*. Sixty identical subunits self-assemble into a thermostable, 25 nm diameter dodecahedron cage with three exposed N-terminal monomer loops at each of the twenty vertices. Staphylococcal Sortase A (SrtA) mediated ligation can be used to functionalize E2 nanoparticles with a variety of proteins and polypeptides, including ELP. Z-ELP functionalized E2 nanoparticles offer unprecedented potential for affinity precipitation of proteins due to its enlarged dimension and enhanced multi-valent interaction with antibodies.

SUMMARY OF THE INVENTION

The present invention relates to nanoparticles and their uses for purifying target proteins by affinity precipitation.

A nanoparticle comprising a fusion protein and a scaffolding domain is provided. The fusion protein is covalently bound to the scaffolding domain. The fusion protein comprises an affinity domain specific for a target protein and a stimuli responsive precipitation domain. The scaffolding domain comprises self-assembled proteins and has a diameter of at least 10 nm. The nanoparticle is soluble in a first solution in the absence of the target protein. The nanoparticle is, capable of binding specifically to the target protein in the first solution and precipitating with the target protein out of the first solution in response to a first stimulus. The first stimulus comprises addition of the target protein to the first solution.

In one embodiment, the first stimulus consists of addition of the target protein to the first solution, the first solution has a temperature of 15-25° C., a salt concentration of 50-200 mM and a pH of pH 6-9, and the molar ratio of the affinity domain to the target protein in the first solution is in the range of 3:1-6:1.

The first stimulus may further comprise a change to the first solution. The change to the first solution may be selected from the group consisting of a change of temperature of the first solution, a change of salt concentration of the first solution, a change of pH of the first solution and a combination thereof. The salt may have a cation selected from the group consisting of ammonium, potassium and sodium. The salt may have an anion selected from the group consisting of phosphate, sulfate, carboxylate and chloride.

In one embodiment, the first solution has a temperature of 15-25° C. and the first stimulus excludes the change to temperature of the first solution. In another embodiment, the first solution has a temperature of 15-25° C. and the first stimulus further comprises a change of temperature of the first solution of no more than 10° C.

In one embodiment, the first solution has a salt concentration of 50-200 mM, and the first stimulus excludes a change of salt concentration of the first solution. In another embodiment, the first solution has a salt concentration of 50-200 mM, and the first stimulus further comprises a change of salt concentration of the first solution of no more than 1 M.

In one embodiment, the first solution has a pH of pH 6-9, and the first stimulus excludes a change to pH of the first solution. In another embodiment, the first solution has a pH of pH 6-9, and the first stimulus further comprises a change of pH of the first solution of no more than 5 pH units.

The precipitated nanoparticle may be capable of being solubilized in a second solution to release the target protein from the nanoparticle in the second solution in response to a second stimulus. The second stimulus may be selected from the group consisting of a change of temperature of the second solution, a change of salt concentration of the second solution, a change of pH of the second solution and a combination thereof. The second stimulus may be a change of temperature of the second solution to less than 25° C. The second stimulus may be a change of salt concentration of the second solution to less than 200 mM. The second stimulus may be a change of pH of the second solution to less than pH 4.

The target protein may be an antibody or an antigen-binding fragment thereof. The antibody may be selected from the group consisting of immunoglobulin (Ig) types IgG, IgD, IgE, IgA and IgM.

The affinity domain may be selected from the group consisting of Z-domain, protein A, protein G, protein L, protein M, single-chain variable fragment (scFv) domain, fibronectin type III (Fn III) domain and a combination thereof.

The precipitation domain may be selected from the group consisting of elastin-like polypeptides (ELPs), resilin-like polypeptides (RLPs), elastin-mimetic polypeptides, tropoelastin-based polypeptides and a combination thereof.

The scaffolding domain may consist of self-assembled proteins. The self-assembled proteins may be selected from the group consisting of E2 core of pyruvate dehydrogenase, lumazine synthase, ferritin, encapsulin, virus-like particles (VLPs), and a combination thereof. The scaffolding domain may consist of E2 core of pyruvate dehydrogenase from *Bacillus stearothermophilus*. The scaffolding domain may consist of a virus like particle from human hepatitis B virus (HBV). The scaffolding domain may have a diameter of at least 24 nm.

In one embodiment, the affinity domain consists of Z-domain, the precipitation domain consists of elastin-like polypeptides (ELPs), and the scaffolding domain consists of E2 core of pyruvate dehydrogenase.

A composition comprising a nanoparticle in a first solution is provided. The nanoparticle comprises a fusion protein and a scaffolding domain. The fusion protein is covalently bound to the scaffolding domain. The fusion protein comprises an affinity domain specific for a target protein and a stimuli responsive precipitation domain. The scaffolding domain comprises self-assembled proteins and has a diameter of at least 10 nm. The nanoparticle is soluble in the first solution in the absence of the target protein. The nanoparticle is capable of binding specifically to the target protein in the first solution and precipitating with the target protein out of the first solution in response to a first stimulus. The first stimulus comprises addition of the target protein to the first solution. In one embodiment, the first stimulus consists of addition of the target protein to the first solution, the first solution has a temperature of 15-25° C., a salt concentration of 50-200 mM and a pH of pH 6-9, and the molar ratio of the affinity domain to the target protein in the first solution is in the range of 3:1-6:1. The first stimulus may further comprise a change to the first solution. The change to the first solution may be selected from the group consisting of a change of temperature of the first solution, a change of salt concentration of the first solution, a change of pH of the first solution and a combination thereof. The precipitated nanoparticle may be capable of being solubilized in a second solution to release the target protein from the nanoparticle in the second solution in response to a second stimulus.

A complex comprising a nanoparticle and a target protein is provided. The nanoparticle is bound specifically to the target protein. The nanoparticle comprises a fusion protein and a scaffolding domain. The fusion protein is covalently bound to the scaffolding domain. The fusion protein comprises an affinity domain specific for the target protein and a stimuli responsive precipitation domain. The scaffolding domain comprises self-assembled proteins and has a diameter of at least 10 nm. The complex is capable of precipitating out of a first solution. In one embodiment, the first solution has a temperature of 15-25° C., a salt concentration of 50-200 mM and a pH of pH 6-9, and the molar ratio of the affinity domain to the target protein in the first solution is in the range of 3:1-6:1. The complex may be capable of precipitating out of the first solution in the absence of a change to the first solution. The complex may be capable of precipitating out of the first solution in the presence of a change to the first solution. The change to the first solution may be selected from the group consisting of a change of temperature of the first solution, a change of salt concentration of the first solution, a change of pH of the first solution and a combination thereof. The precipitated complex may be capable of being solubilized in a second solution to release the target protein from the nanoparticle in the second solution in response to a stimulus.

A composition comprising a complex in a first solution is provided. The complex comprises a nanoparticle and a target protein. The nanoparticle is bound specifically to the target protein. The nanoparticle comprises a fusion protein and a scaffolding domain. The fusion protein is covalently bound to the scaffolding domain. The fusion protein comprises an affinity domain specific for the target protein and a stimuli responsive precipitation domain. The scaffolding domain comprises self-assembled proteins and has a diameter of at least 10 nm. The complex is capable of precipitating out of the first solution. In one embodiment, the first solution has a temperature of 15-25° C., a salt concentration of 50-200 mM and a pH of pH 6-9, and the molar ratio of the affinity domain to the target protein in the first solution is in the range of 3:1-6:1. The complex may be capable of precipitating out of the first solution in the absence of a change to the first solution. The complex may be capable of precipitating out of the first solution in the presence of a change to the first solution. The change to the first solution may be selected from the group consisting of a change of temperature of the first solution, a change of salt concentration of the first solution, a change of pH of the first solution and a combination thereof. The precipitated complex may be capable of being solubilized in a second solution to release the target protein from the nanoparticle in the second solution in response to a stimulus.

A method for purifying a target protein produced by host cells without chromatography is provided. The purification method comprises (a) separating the target protein from the host cells; (b) exposing the separated target protein to a nanoparticle in a first solution to form a complex of the target protein and the nanoparticle, wherein the nanoparticle comprises a fusion protein and a scaffolding domain, wherein the fusion protein is covalently bound to the scaffolding domain, wherein the fusion protein comprises an affinity domain specific for the target protein and a stimuli responsive precipitation domain, wherein the nanoparticle is bound specifically to the target protein, wherein the scaffolding domain comprises self-assembled proteins and has a diameter of at least 10 nm, whereby the complex precipitates out of the first solution; (c) adding the precipitated complex to a second solution; and (d) applying a stimulus to solubilize the precipitated complex in the second solution and release the target protein from the nanoparticle in the second solution, whereby the target protein is purified from the host cells. At least 95% by weight of the target protein produced by the host cells may be purified from the host cells. At least 5% by weight of the target protein produced by the host cells may be purified from the host cells using the nanoparticle more than that using a control particle. The purified target protein may have a purity of at least 99% by weight.

In one embodiment of the purification method, the first solution has a temperature of 15-25° C., a salt concentration of 50-200 mM and a pH of pH 6-9, wherein the molar ratio of the affinity domain to the target protein in the first solution is in the range of 3:1-6:1.

According to the purification method, the complex may precipitate out of the first solution in the absence of a change to the first solution in step (b).

According to the purification method, the complex may precipitate out of the first solution in the presence of a change to the first solution in step (b). The change to the first solution may be selected from the group consisting of a change of temperature of the first solution, a change of salt concentration of the first solution, a change of pH of the first solution, and a combination thereof.

According to the purification method, the stimulus may be selected from the group consisting of a change of temperature of the second solution, a change of salt concentration of the second solution, a change of pH of the second solution and a combination thereof. The stimulus may be a change of temperature of the second solution to less than 25° C. The stimulus may be a change of salt concentration of the second solution to less than 200 mM. The stimulus may be a change of pH of the second solution to less than pH 4. The second solution in step (c) may have a pH greater than pH 4.

According to the purification method, the target protein may be an antibody or an antigen-binding fragment thereof. The antibody may be selected from the group consisting of immunoglobulin (Ig) types IgG, IgD, IgE, IgA and IgM.

According to the purification method, the host cells may be selected from the group consisting of Chinese hamster ovary (CHO) cells, *Escherichia co/i* cells, *Saccharomyces cerevisiae* cells, *Pichia pastoris* cells, and Human embryonic kidney (HEK) cells.

A composition comprising a target protein purified by the purification method of the present invention is provide. The composition may further comprise a pharmaceutically acceptable excipient. The composition may further comprise a diagnostically acceptable excipient.

A method for preparing a nanoparticle of the present invention is provided. The preparation method comprises (a) making a fusion protein comprising an affinity domain specific for a target protein and a stimuli responsive precipitation domain; and (b) conjugating the fusion protein covalently to a scaffolding domain to generate a nanoparticle, wherein the scaffolding domain comprises self-assembled proteins and has a diameter of at least 10 nm, wherein the fusion protein is covalently bound to the scaffolding domain, and wherein the nanoparticle is soluble in a first solution in the absence of the target protein, wherein the nanoparticle is capable of binding specifically to the target protein in the first solution and precipitating with the target protein out of the first solution in response to a first stimulus, and wherein the first stimulus comprises addition of the target protein to the first solution. The precipitated nanoparticle may be capable of being solubilized in a second solution to release the target protein from the nanoparticle in the second solution in response to a second stimulus. The target protein may be expressed in *Escherichia co/i*.

Step (b) of the preparation method may comprise post-translational bacterial sortase A mediated ligation.

In one embodiment of the preparation method, the first stimulus consists of addition of the target protein to the first solution, the first solution has a temperature of 15-25° C., a salt concentration of 50-200 mM and a pH of pH 6-9, and the molar ratio of the affinity domain to the target protein in the first solution is in the range of 3:1-6:1.

According to the preparation method, the first stimulus may further comprise a change to the first solution. The change to the first solution may be selected from the group consisting of a change of temperature of the first solution, a change of salt concentration of the first solution, a change of pH of the first solution and a combination thereof.

According to the preparation method, the second stimulus may be selected from the group consisting of a change of temperature of the second solution, a change of salt concentration of the second solution, a change of pH of the second solution and a combination thereof.

DETAILED DESCRIPTION OF THE INVENTION

Figure 1:
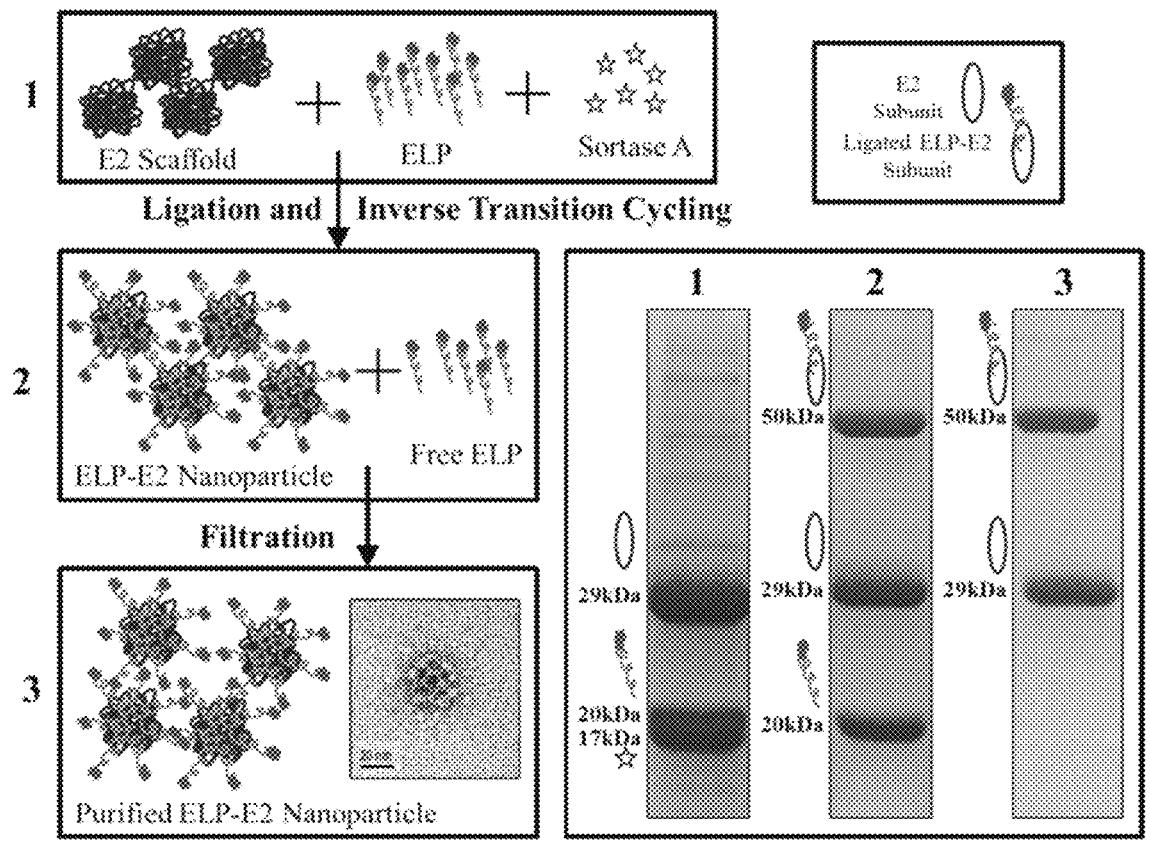
FIG. 1 shows ELP ligation to E2 scaffold. Step 1: Purified ELP-LPETG (20 kDa) and GGG-E2 (29 kDa) is mixed with SrtA (17 kDa) lysate in a reaction buffer. Step 2: SrtA catalyzes conjugation of ELP to E2 and generates ELP-E2 ligation product (50 kDa). Nanoparticle is purified by ELP ITC. Step 3: 100 kDa filtration removes any unreacted ELP resulting in a highly pure, stable ELP-E2 nanoparticle. 2% uranyl acetate stained TEM image of purified nanoparticle also shown. Each step is represented by a corresponding Coomassie stained 10% acrylamide reduced SDS-PAGE gel image.

The present invention provides nanoparticles comprising a scaffolding domain and a fusion protein of an affinity domain and a precipitation domain and the uses of the nanoparticles for affinity precipitation of target proteins. The invention is based on the discovery that affinity precipitation can be significantly enhanced by enlarging the dimension of a capturing scaffold. Conjugating affinity-biopolymer fusion proteins to a nanometer scale scaffold has been found to precipitate to insoluble aggregates at significantly lower temperatures and/or salt concentrations than equal concentrations of the affinity-biopolymer fusion protein free in solution. After the nanoparticles bind and precipitate target proteins, the target proteins may be released from the precipitated nanoparticles. The nanoparticles may then be solubilized and recycled for precipitating additional target proteins.

The terms "protein" and "polypeptide" are used herein interchangeably, and refer to a polymer of amino acid residues with no limitation with respect to the minimum length of the polymer. Preferably, the protein or polypeptide has at least 20 amino acid residues. The definition includes both full-length proteins and fragments thereof, as well as modifications thereof (e.g., glycosylation, phosphorylation, deletions, additions and substitutions). The protein may be an antibody. The protein may be produced by host cells.

The term "polynucleotide" used herein refers to a polymer of nucleotide residues with no limitation with respect to the minimum length of the polymer. Preferably, the polynucleotide has at least 60 nucleotides. The polynucleotide may be a DNA, cDNA or RNA molecule. A polynucleotide may comprise a nucleotide sequence encoding a target protein (e.g., an antibody) under control of a promoter, for example, an inducible promoter.

The term "variant" of a protein or polynucleotide used herein refers to a polypeptide having an amino acid or nucleic acid sequence that is the same as the amino acid or nucleic acid sequence of the protein or polynucleotide except having at least one amino acid or nucleic acid modified, for example, deleted, inserted, or replaced, respectively. A variant of a protein or polynucleotide may have an amino acid or nucleic acid sequence at least about 80%, 90%, 95%, or 99%, preferably at least about 90%, more preferably at least about 95%, identical to the corresponding amino acid sequence or nucleic acid of the protein or polynucleotide.

The term "derived from" used herein refers to the origin or source, and may include naturally occurring (i.e., native) and non-naturally occurring (i.e., recombinant) microorganisms or molecules, or variants thereof. For example, a protein derived from a microbe (e.g., a bacterium) may be identical to the corresponding native protein or a variant thereof in the microbe, for example, having an amino acid sequence at least about 70%, 80%, 90%, 95%, or 99% identical to the corresponding native protein. A gene derived from a microbe (e.g., a bacterium) may be identical to the corresponding native gene or a variant thereof in the microbe, for example, having a nucleic acid sequence at least about 80%, 90%, 95%, or 99% identical to the corresponding native gene.

The term "antibody" as used herein refers to an immunoglobulin (Ig) molecule, an antigen binding fragment thereof or a binding derivative thereof. An antigen binding fragment of an antibody contains an antigen binding site that specifically binds an antigen. The antibodies (Abs) may be monoclonal antibodies, polyclonal antibodies or multispecific antibodies (e.g., bispecific antibodies). Examples of antibodies include immunoglobulin (Ig) types IgG, IgD, IgE, IgA and IgM. The antibodies may be native antibodies or recombinant antibodies. The antibodies may be produced by host cells.

The term "fusion protein" as used herein refers to a protein comprising two or more polypeptides that are derived from different proteins but expressed from a polynucleotide comprising a nucleotide sequence encoding the fusion protein under control of a single promoter.

The term "nanoparticle" as used herein refers to a particle having a diameter in the range from about 10 nm to about 1,000 nm. The nanoparticles may comprise core proteins that form the core of the nanoparticle, and optional surface proteins that are on the surface of the nanoparticle. The core proteins may be self-assembled proteins. The surface proteins may have been covalently bound to the core proteins by post-translational modifications.

The term "self-assembled proteins" as used herein refers to a unit of proteins formed spontaneously by the proteins themselves through protein-protein interactions. The self-assembled proteins may have a diameter of at least about 1, 5, 10, 20, 24, 25, 30, 40, 50, 75 or 100 nm, or about 10-100 nm, 5-50 nm, 10-50 nm or 10-25 nm. In one embodiment, the self-assembled proteins have a diameter of at least about 10 nm. In another embodiment, the self-assembled proteins have a diameter of at least about 24 nm.

The self-assembled proteins may be formed by identical proteins or different proteins. Examples of the self-assembled proteins include E2 core of the pyruvate dehydrogenase complex, lumazine synthase, ferritin, encapsulin and virus-like particles (VLPs). The E2 core of pyruvate dehydrogenase complex is also known as dihydrolipoyl transacetylase. The E2 core of pyruvate dehydrogenase may be from *Bacillus stearothermophilus*. The virus like particle may be from human hepatitis B virus (HBV).

The nanoparticle may be functionalized. The term "functionalized nanoparticle" refer to a nanoparticle that has a biological function or is biologically active. For example, the nanoparticle may be capable of binding specifically a target protein (e.g., an antibody) because a biologically active protein on the surface of the nanoparticle and conjugated post-translationally to the core proteins in the nanoparticle. In one embodiment of such a functionalized nanoparticle, a protein specific for an antibody is covalently conjugated to the E2 core of the pyruvate dehydrogenase complex. The conjugation may be carried out by Sortase-A mediated ligation.

The term "ligated fusion protein" used herein refers to a fusion protein, for example, comprising an affinity domain (e.g., Z domain) and a precipitation domain (e.g., ELP), that is conjugated to a scaffolding domain (e.g., E2 core of the pyruvate dehydrogenase complex). The ligated fusion protein and the scaffolding domain may form a nanoparticle, and the ligated fusion protein may be on the surface of the nanoparticle. In one embodiment, the ligated fusion protein is Z-ELP conjugated to the surface of the E2 core of the pyruvate dehydrogenase complex (E2).

The term "free fusion protein" used herein refers to a fusion protein, for example, comprising an affinity domain (e.g., Z domain) and a precipitation domain (e.g., ELP), that is not conjugated to a scaffolding domain (e.g., E2). In one embodiment, "free Z-ELP" is fusion protein Z-ELP that is not conjugated to a scaffolding domain.

To compare a free fusion protein (e.g., Z-ELP) with its corresponding ligated fusion protein (e.g., Z-ELP-E2), the free fusion protein and its corresponding ligated fusion protein are used in an equal molar concentration. In this embodiment, the effect of the molar concentration of free Z-ELP may be compared to that of an equal molar concentration of ligated Z-ELP (e.g., Z-ELP-E2).

The term "phase transition" used herein refers to a change of a material (e.g., a polypeptide or protein, a nanoparticle, or a complex of a nanoparticle and a protein) between a soluble phase and an insoluble phase in a solution. The phase transition may be reversible or irreversible. The phase transition may be triggered by one or more stimuli. The stimulus may be any change external to the material that triggers phase transition of the material. The stimulus may be addition of a target protein to the solution, in which the material binds specifically the target protein, with or without any change to the solution.

The change to the solution may be selected from the group consisting of a change of temperature of the solution, a change of salt concentration of the solution, a change of pH of the solution, and a combination thereof. The change (e.g., elevation or reduction) of temperature of the solution may be no more than about 50, 40, 30, 20, 10 or 5° C. The change (e.g., elevation or reduction) of salt concentration of the solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH may be no more than 10, 9, 8, 7, 6, 5, 4, 3 or 2 pH units.

The present invention provides a nanoparticle comprising a fusion protein and a scaffolding domain. The fusion protein is covalently bound to the scaffolding domain. The fusion protein comprises an affinity domain specific for a target protein and a stimuli responsive precipitation domain. The scaffolding domain comprises self-assembled proteins and has a diameter of at least about 1, 5, or 10 nm. The nanoparticle is soluble in a first solution in the absence of the target protein. The nanoparticle is capable of binding specifically to the target protein in the first solution and precipitating with the target protein out of the first solution in response to a first stimulus. The first stimulus comprises addition of the target protein to the first solution.

The precipitated nanoparticle may be capable of being solubilized in a second solution to release the target protein from the nanoparticle in the second solution in response to a second stimulus.

The affinity domain may be any ligand polypeptide capable of binding specifically a target protein or a binding derivative thereof. A binding derivative of a ligand polypeptide is capable of binding specifically the same target protein as the ligand polypeptide. The affinity domain may have a dissociation constant of less than about 100, 50, 25, 10, 5, 1 or 0.1 µM for the target protein. The binding derivative of a ligand polypeptide may have a binding affinity of at least about 70%, 80%, 90%, 95% or 99% of the binding affinity of the ligand peptide for the same target protein. The binding derivative of a ligand polypeptide may have an amino acid sequence at least about 70%, 80%, 90%, 95% or 99% identical to that of the ligand polypeptide. Examples of the affinity domains include Z-domain, protein A, protein G, protein L, protein M, single-chain variable fragment (scFv) domain, fibronectin type III (Fn III) domain, a binding derivative thereof, and a combination thereof.

The target protein may be any protein of interest. For example, the target protein may be an antibody or an antigen binding fragment thereof. The antibody may be a monoclonal antibody. The antibody may be an IgG, IgD, IgE, IgA or IgM. The antibody may be human IgG1 or IgG4.

The stimuli responsive precipitation domain may be any polypeptide that precipitates, or changes from a soluble phase to an insoluble phase, in a solution in responsive to one or more stimuli. The precipitation may be reversible or irreversible. The stimulus may be a change to the solution. The change to the solution may be a change of temperature of the solution, a change of salt concentration of the solution, a change of pH of the solution, or a combination thereof. The stimulus may exclude a change to temperature of the solution. The change (e.g., elevation or reduction) of temperature of the solution may be no more than about 50, 40, 30, 20, 10 or 5° C. The change (e.g., elevation or reduction) of salt concentration of the solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH may be no more than about 10, 9, 8, 7, 6, 5, 4, 3 or 2 pH units. Examples of the precipitation domain include elastin-like polypeptides (ELPs), resilin-like polypeptides (RLPs), elastin-mimetic polypeptides, tropoelastin-based polypeptides and a combination thereof.

The scaffolding domain, also called scaffold, may consist of self-assembled proteins selected from the group consisting of E2 core of the pyruvate dehydrogenase complex (or dihydrolipoyl transacetylase), lumazine synthase, ferritin, encapsulin, virus-like particles (VLPs), and a combination thereof. The E2 core of pyruvate dehydrogenase may be from *Bacillus stearothermophilus*. The virus like particle may be from human hepatitis B virus (HBV). In one embodiment, the scaffolding domain consists of the Z-ELP functionalized E2 core of pyruvate dehydrogenase from *Bacillus stearothermophilus*. In another embodiment, the scaffolding domain consists of a virus like particle from human hepatitis B virus (HBV). The scaffolding domain may have a diameter of at least about 1, 5, 10, 20, 24, 25, 30, 40, 50, 75 or 100 nm, or about 10-100 nm, 5-50 nm, 10-50 nm or 10-25 nm. In one embodiment, the scaffolding domain has a diameter of at least about 10 nm. In another embodiment, the scaffolding domain has a diameter of at least about 24 nm. The nanoparticle may precipitate with the target protein quickly, for example, within about 1, 5, 10, 30, 60 or 120 minutes, after the change to the solution.

In some embodiments, the first stimulus consists of addition of the target protein to the first solution, the first solution has a temperature of about 5-35° C., 10-35° C., 15-35° C., 5-25° C., 10-25° C. or 15-25° C., a salt concentration of about 1-1,000 mM, 5-500 mM, 10-500 mM, 50-500 mM, 50-200 mM, 100-200 mM, 50-150 mM or 100-150 mM and a pH of about pH 4-11, 5-10, 6-9 or 6-8, and the molar ratio of the affinity domain to the target protein in the first solution is in the range of about 10:1-1:10, 6:1-1:6, 3:1-6:1 or 3:1-1:3. In one embodiment, the first stimulus consists of addition of the target protein to the first solution, the first solution has a temperature of about 15-25° C., a salt concentration of about 50-200 mM and a pH of about pH 6-9, and the molar ratio of the affinity domain to the target protein in the first solution is in the range of about 3:1-6:1.

The first stimulus may further comprise a change to the first solution. The change to the first solution may be a change of temperature of the first solution, a change of salt concentration of the first solution, a change of pH of the first solution or a combination thereof. The first stimulus may exclude a change to temperature of the first solution. The change (e.g., elevation or reduction) of temperature of the first solution may be no more than about 50, 40, 30, 20, 10 or 5° C. The change (e.g., elevation or reduction) of salt concentration of the first solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the first solution may be no more than about 10, 9, 8, 7, 6, 5, 4, 3 or 2 pH units.

In some embodiments, the first solution has a temperature of about 5-35° C., 10-35° C., 15-35° C., 5-25° C., 10-25° C. or 15-25° C., and the first stimulus excludes a change to temperature of the first solution. In one specific embodiment, the first solution has a temperature of about 15-25° C., and the first stimulus excludes the change to temperature of the first solution.

In some embodiments, the first solution has a temperature of about 5-35° C., 10-35° C., 15-35° C., 5-25° C., 10-25° C. or 15-25° C., and the first stimulus further comprises a change of temperature of the first solution of no more than about 20, 15, 10 or 5° C. In one specific embodiment, the first solution has a temperature of about 15-25° C., and the first stimulus further comprises a change of temperature of the first solution of no more than about 10° C.

In some embodiments, the first solution has a salt concentration of about 1-1,000 mM, 5-500 mM, 10-500 mM, 50-500 mM, 50-200 mM, 100-200 mM, 50-150 mM or 100-150 mM, and the first stimulus excludes a change of salt concentration of the first solution. In one specific embodiment, the first solution has a salt concentration of about 50-200 mM, and the first stimulus excludes a change of salt concentration of the first solution.

In some embodiments, the first solution has a salt concentration of about 1-1,000 mM, 5-500 mM, 10-500 mM, 50-500 mM, 50-200 mM, 100-200 mM, 50-150 mM or 100-150 mM, and the first stimulus further comprises a change of salt concentration of the first solution of no more than about 5, 4, 3, 2, 1, 0.5 or 0.1 M. In one specific embodiment, the first solution has a salt concentration of about 50-200 mM, and the first stimulus further comprises a change of salt concentration of the first solution of no more than about 1 M.

In some embodiments, the first solution has a pH of about pH 4-11, 5-10, 6-9 or 6-8, and the first stimulus excludes a change to pH of the first solution. In one specific embodiment, the first solution has a pH of about pH 6-9, and the first stimulus excludes a change to pH of the first solution.

In some embodiments, the first solution has a pH of about pH 4-11, 5-10, 6-9 or 6-8, and the first stimulus further comprises a change of pH of the first solution of no more than about 10, 9, 8, 7, 6, 5, 4, 3 or 2 pH units. In one specific embodiment, the first solution has a pH of about pH 6-9, and the first stimulus further comprises a change of pH of the first solution of no more than about 5 pH units.

The second stimulus may be a change to the second solution. The change to the second solution may be a change of temperature of the second solution, a change of salt concentration of the second solution, a change of pH of the second solution or a combination thereof. The second stimulus may exclude a change to temperature of the solution. The change (e.g., elevation or reduction) of temperature of the second solution may be no more than about 50, 40, 30, 20, 10 or 5° C. The change (e.g., elevation or reduction) of salt concentration of the second solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the second solution may be no more than 10, 9, 8, 7, 6, 5, 4, 3 or 2 pH units.

The second stimulus may be a change of temperature of the second solution to less than about 37, 35, 30, 25, 20, 15, 10, 5 or 4° C. In one embodiment, the second stimulus is a change of temperature of the second solution to less than about 25° C.

The second stimulus may be a change of salt concentration of the second solution to less than about 1,000, 500, 200, 150 or 100 mM. In one embodiment, the second stimulus is a change of salt concentration of the second solution to less than about 200 mM.

The second stimulus may be a change of pH of the second solution to less than about pH 7, 6, 5, 4, 3 or 2. In one embodiment, the second stimulus is a change of pH of the second solution to less than about pH 4.

Upon precipitation, aggregates of the nanoparticle and the target protein may be formed. The aggregates may be visible or have a diameter of at least about 100, 200, 500, 1000, 2000, 5000 or 10,000 nm. The precipitation may be reversed by removal of the change or solubilization of the precipitated nanoparticle. Upon reversal of the precipitation, the target protein may be removed from the nanoparticle. The nanoparticle maybe solubilized and recycled for precipitating another target protein.

In some embodiments, the affinity domain consists of Z-domain, the precipitation domain consists of elastin-like polypeptides (ELPs), and the scaffolding domain consists of E2 core of pyruvate dehydrogenase.

In other embodiments, the affinity domain consists of Z-domain, the precipitation domain consists of elastin-like polypeptides (ELPs), and the scaffolding domain consists of a viral capsid of HBV.

For each nanoparticle of the present, a composition comprising the nanoparticle in a first solution is provided. The nanoparticle comprises a fusion protein and a scaffolding domain. The fusion protein is covalently bound to the scaffolding domain. The fusion protein comprises an affinity domain specific for a target protein and a stimuli responsive precipitation domain. The scaffolding domain comprises self-assembled proteins and has a diameter of at least about 1, 5, or 10 nm. The nanoparticle is soluble in the first solution in the absence of the target protein. The nanoparticle is capable of binding specifically to the target protein in the first solution and precipitating with the target protein out of the first solution in response to a first stimulus. The first stimulus comprises addition of the target protein to the first solution. In one embodiment, the first stimulus consists of addition of the target protein to the first solution, which has a temperature of about 15-25° C., a salt concentration of about 50-200 mM and a pH of about pH 6-9, and the molar ratio of the affinity domain to the target protein in the first solution is in the range of about 3:1-6:1. The first stimulus may further comprise a change to the solution. The change to the first solution may be selected from the group consisting of a change of temperature of the solution, a change of salt concentration of the solution, a change of pH of the first solution and a combination thereof. The change (e.g., elevation or reduction) of temperature of the first solution may be no more than about 50, 40, 30, 20, 10 or 5° C. The change (e.g., elevation or reduction) of salt concentration of the first solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the first solution may be no more than 10, 9, 8, 7, 6, 5, 4, 3 or 2 pH units.

The precipitated nanoparticle out of the first solution may be capable of being solubilized in a second solution to release the target protein from the nanoparticle in the second solution in response to a second stimulus. The second stimulus may be a change to the second solution. The change to the second solution may be a change of temperature of the second solution, a change of salt concentration of the second solution, a change of pH of the second solution or a combination thereof. The second stimulus may exclude a change to temperature of the solution. The change (e.g., elevation or reduction) of temperature of the second solution may be no more than about 50, 40, 30, 20, 10 or 5° C. The change (e.g., elevation or reduction) of salt concentration of the second solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the second solution may be no more than 10, 9, 8, 7, 6, 5, 4, 3 or 2 pH units. The second stimulus may be a change of temperature of the second solution to less than about 37, 35, 30, 25, 20, 15, 10, 5 or 4° C. In one embodiment, the second stimulus is a change of temperature of the second solution to less than about 25° C. The second stimulus may be a change of salt concentration of the second solution to less than about 1,000, 500, 200, 150 or 100 mM. In one embodiment, the second stimulus is a change of salt concentration of the second solution to less than about 200 mM. The second stimulus may be a change of pH of the second solution to less than about pH 7, 6, 5, 4, 3 or 2. In one embodiment, the second stimulus is a change of pH of the second solution to less than about pH 4.

The present invention also provides a complex comprising a nanoparticle of the present invention and a target protein. The nanoparticle is bound specifically to the target protein. The nanoparticle comprises a fusion protein and a scaffolding domain. The fusion protein is covalently bound to the scaffolding domain. The fusion protein comprises an affinity domain specific for the target protein and a stimuli responsive precipitation domain. The scaffolding domain comprises self-assembled proteins and have a diameter of at least about 1, 5, or 10 nm. The complex is capable of precipitating out of a first solution.

The complex may precipitate out of the first solution in the absence of a change to the first solution. The first solution may have a temperature of about 5-35° C., 10-35° C., 15-35° C., 5-25° C., 10-25° C. or 15-25° C., a salt concentration of about 1-1,000 mM, 5-500 mM, 10-500 mM, 50-500 mM, 50-200 mM, 100-200 mM, 50-150 mM or 100-150 mM and a pH of about pH 4-11, 5-10, 6-9 or 6-8, and the molar ratio of the affinity domain to the target protein in the first solution may be in the range of about 10:1-1:10, 6:1-1:6, 3:1-6:1 or 3:1-1:3. In one embodiment, the first solution has a temperature of about 15-25° C., a salt concentration of about 50-200 mM and a pH of about pH 6-9, and the molar ratio of the affinity domain to the target protein in the first solution is in the range of about 3:1-6:1.

The complex may precipitate out of the first solution in the presence of a change to the first solution. The change of temperature of the first solution, a change of salt concentration of the first solution, a change of pH of the first solution and a combination thereof. The change (e.g., elevation or reduction) of temperature of the first solution may be no more than about 50, 40, 30, 20, 10 or 5° C. The change (e.g., elevation or reduction) of salt concentration of the first solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the first solution may be no more than 10, 9, 8, 7, 6, 5, 4, 3 or 2 pH units.

The precipitated complex may be capable of being solubilized in a second solution to release the target protein from the nanoparticle in the second solution in response to a stimulus. The stimulus may be a change to the second solution. The change to the second solution may be a change of temperature of the second solution, a change of salt concentration of the second solution, a change of pH of the second solution or a combination thereof. The stimulus may exclude a change to temperature of the solution. The change (e.g., elevation or reduction) of temperature of the second solution may be no more than about 50, 40, 30, 20, 10 or 5° C. The change (e.g., elevation or reduction) of salt concentration of the second solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the second solution may be no more than 10, 9, 8, 7, 6, 5, 4, 3 or 2 pH units. The stimulus may be a change of temperature of the second solution to less than about 37, 35, 30, 25, 20, 15, 10, 5 or 4° C. In one embodiment, the stimulus is a change of temperature of the second solution to less than about 25° C. The stimulus may be a change of salt concentration of the second solution to less than about 1,000, 500, 200, 150 or 100 mM. In one embodiment, the stimulus is a change of salt concentration of the second solution to less than about 200 mM. The stimulus may be a change of pH of the second solution to less than about pH 7, 6, 5, 4, 3 or 2. In one embodiment, the stimulus is a change of pH of the second solution to less than about pH 4.

For each complex of the present invention, a composition comprising the complex in a first solution is provided. The complex comprises a nanoparticle and a target protein. The nanoparticle is bound specifically to the target protein. The nanoparticle comprises a fusion protein and a scaffolding domain. The fusion protein is covalently bound to the scaffolding domain. The fusion protein comprises an affinity domain specific for the target protein and a stimuli responsive precipitation domain. The scaffolding domain comprises self-assembled proteins and have a diameter of at least about 1, 5, or 10 nm. The complex is capable of precipitating out of the first solution.

For the complex of the present invention, the complex may precipitate out of the first solution in the absence of a change to the first solution. The first solution may have a temperature of about 5-35° C., 10-35° C., 15-35° C., 5-25° C., 10-25° C. or 15-25° C., a salt concentration of about 1-1,000 mM, 5-500 mM, 10-500 mM, 50-500 mM, 50-200 mM, 100-200 mM, 50-150 mM or 100-150 mM and a pH of about pH 4-11, 5-10, 6-9 or 6-8, and the molar ratio of the affinity domain to the target protein in the first solution may be in the range of about 10:1-1:10, 6:1-1:6, 3:1-6:1 or 3:1-1:3. In one embodiment, the first solution has a temperature of about 15-25° C., a salt concentration of about 50-200 mM and a pH of about pH 6-9, and the molar ratio of the affinity domain to the target protein in the first solution is in the range of about 3:1-6:1.

For the complex of the present invention, the complex may precipitate out of the first solution in the presence of a change to the first solution. The change of temperature of the first solution, a change of salt concentration of the first solution, a change of pH of the first solution and a combination thereof. The change (e.g., elevation or reduction) of temperature of the first solution may be no, more than about 50, 40, 30, 20, 10 or 5° C. The change (e.g., elevation or reduction) of salt concentration of the first solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the first solution may be no more than 10, 9, 8, 7, 6, 5, 4, 3 or 2 pH units.

After the complex of the present invention precipitates, the precipitated complex may be capable of being solubilized in a second solution to release the target protein from the nanoparticle in the second solution in response to a stimulus. The stimulus may be a change to the second solution. The change to the second solution may be a change of temperature of the second solution, a change of salt concentration of the second solution, a change of pH of the second solution or a combination thereof. The stimulus may exclude a change to temperature of the solution. The change (e.g., elevation or reduction) of temperature of the second solution may be no more than about 50, 40, 30, 20, 10 or 5° C. The change (e.g., elevation or reduction) of salt concentration of the second solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the second solution may be no more than 10, 9, 8, 7, 6, 5, 4, 3 or 2 pH units. The stimulus may be a change of temperature of the second solution to less than about 37, 35, 30, 25, 20, 15, 10, 5 or 4° C. In one embodiment, the stimulus is a change of temperature of the second solution to less than about 25° C. The stimulus may be a change of salt concentration of the second solution to less than about 1,000, 500, 200, 150 or 100 mM. In one embodiment, the stimulus is a change of salt concentration of the second solution to less than about 200 mM. The stimulus may be a change of pH of the second solution to less than about pH 7, 6, 5, 4, 3 or 2. In one embodiment, the stimulus is a change of pH of the second solution to less than about pH 4.

The present invention further provides a method for purifying a target protein produced by host cells without chromatography. The method comprises (a) separating the target protein from the host cells, and (b) exposing the separated target protein to a nanoparticle of the present invention in a first solution to form a complex of the target protein and the nanoparticle. The nanoparticle comprises a fusion protein and a scaffolding domain. The fusion protein is covalently bound to the scaffolding domain. The fusion protein comprises an affinity domain specific for the target protein and a stimuli responsive precipitation domain. The nanoparticle is bound specifically to the target protein. The scaffolding domain comprises self-assembled proteins and have a diameter of at least about 1, 5, or 10 nm. The complex precipitates out of the first solution. The method further comprises (c) adding the precipitated complex to a second solution, and (d) applying a stimulus to solubilize the precipitated complex in the second solution and release the target protein from the nanoparticle in the second solution. As a result, the target protein is purified from the host cells.

According to the purification method of the present invention, at least about 70%, 80%, 90%, 95% or 99% by weight of the target protein produced by the host cells may be purified from the host cells. In one embodiment, at least about 95% by weight of the target protein produced by the host cells is purified from the host cells.

The purification method of the present invention may provide better and quicker purification of target proteins, for example, antibodies, produced by host cells as compared to that purified using just the fusion protein without the scaffolding domain. The nanoparticle may form at least about 100, 200, 500, 1000, 2000, 5000 or 10,000 nm larger sized aggregates than using only the fusion protein in the nanoparticle. To achieve the same protein purification recovery rate or purity, the nanoparticle of the present invention may require 0.1, 0.2, 0.3, 0.4, 0.5, or 1 M less salt for precipitation than using a control particle. A control particle is identical to the nanoparticle of the present invention having only the fusion protein but not the scaffolding domain. A control particle has a substantially smaller size than the nanoparticle of the present invention. The nanoparticle of the present invention may require 2, 4, 6, 8, 10, or 12° C. lower temperature for precipitation than using the control particle. At least more than about 1%, 2%, 3%, 4%, 5%, 10% or 20% by weight of the target protein produced by the host cells may be purified from the host cells using the nanoparticle of the present invention than that using the control particle. The target protein may be purified from the host cells quickly, for example, within about 5, 10, 30, 60 or 120 minutes, after exposing the separated target protein to the nanoparticle of the present invention.

According to the purification method of the present invention, the purified target protein may have a purity of at least about 70%, 80%, 90%, 95% or 99% by weight. In one embodiment, the purified target protein has a purity of at least about 99% by weight.

According to the purification method, the complex may precipitate out of the first solution in the absence of a change to the first solution in step (b). The first solution may have a temperature of about 5-35° C., 10-35° C., 15-35° C., 5-25° C., 10-25° C. or 15-25° C., a salt concentration of about 1-1,000 mM, 5-500 mM, 10-500 mM, 50-500 mM, 50-200 mM, 100-200 mM, 50-150 mM or 100-150 mM and a pH of about pH 4-11, 5-10, 6-9 or 6-8, and the molar ratio of the affinity domain to the target protein in the first solution may be in the range of about 10:1-1:10, 6:1-1:6, 3:1-6:1 or 3:1-1:3. In one embodiment, the first solution has a temperature of about 15-25° C., a salt concentration of about 50-200 mM and a pH of about pH 6-9, and the molar ratio of the affinity domain to the target protein in the first solution is in the range of about 3:1-6:1.

According to the purification method, the complex may precipitate out of the first solution in the presence of a change to the first solution in step (b). The change of temperature of the first solution, a change of salt concentration of the first solution, a change of pH of the first solution and a combination thereof. The change (e.g., elevation or reduction) of temperature of the first solution may be no more than about 50, 40, 30, 20, 10 or 5° C. The change (e.g., elevation or reduction) of salt concentration of the first solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the first solution may be no more than 10, 9, 8, 7, 6, 5, 4, 3 or 2 pH units.

In the purification method, the stimulus may be a change to the second solution, which may be a change of temperature of the second solution, a change of salt concentration of the second solution, a change of pH of the second solution or a combination thereof. The change (e.g., elevation or reduction) of temperature of the second solution may be no more than about 50, 40, 30, 20, 10 or 5° C. The change (e.g., elevation or reduction) of salt concentration of the second solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the second solution may be no more than 10, 9, 8, 7, 6, 5, 4, 3 or 2 pH units. The stimulus may be a change of temperature of the second solution to less than about 37, 35, 30, 25, 20, 15, 10, 5 or 4° C. In one embodiment, the stimulus is a change of temperature of the second solution to less than about 25° C. The stimulus may be a change of salt concentration of the second solution to less than about 1,000, 500, 200, 150 or 100 mM. In one embodiment, the stimulus is a change of salt concentration of the second solution to less than about 200 mM. The stimulus may be a change of pH of the second solution to less than about pH 7, 6, 5, 4, 3 or 2. In one embodiment, the stimulus is a change of pH of the second solution to less than about pH 4. The second solution in step (c) may have a pH greater than pH 4.

According to the purification method of the present invention, the target protein may be an antibody or an antigen-binding fragment thereof. The antibody may be selected from the group consisting of immunoglobulin (Ig) types IgG, IgD, IgE, IgA and IgM. The antibody may be human IgG1 or IgG4.

The host cells may be any cells suitable for producing the target protein (e.g., antibody). Examples of host cells include Chinese hamster ovary (CHO) cells, *Escherichia co/i* cells, *Saccharomyces cerevisiae* cells, *Pichia pastoris* cells, and Human embryonic kidney (HEK) cells. In one embodiment, the host cells are CHO cells.

A composition comprising the target protein purified by the method of the present invention is provided. The composition may further comprise a pharmaceutically acceptable excipient. Examples of the pharmaceutically acceptable excipient include buffers, salts, sugars, detergents, or other molecules. The composition may further comprise a diagnostically acceptable excipient. Examples of the diagnostically acceptable excipient include buffers, salts, sugars, detergents, or other molecules.

For each nanoparticle of the present invention, a method for preparing the nanoparticle is provided. The preparation method comprises making a fusion protein comprising an affinity domain specific for a target protein and a stimuli responsive precipitation domain, and conjugating the fusion protein covalently to a scaffolding domain to generate a nanoparticle. The scaffolding domain comprises self-assembled proteins and have a diameter of at least 1, 5, or 10 nm. The fusion protein is covalently bound to the scaffolding domain. The nanoparticle is soluble in a first solution in the absence of the target protein. The nanoparticle is capable of binding specifically to the target protein in the first solution and precipitating with the target protein out of the first solution in response to a first stimulus. The first stimulus comprises addition of the target protein to the first solution. The precipitated nanoparticle may be capable of being solubilized in a second solution to release the target protein from the nanoparticle in the second solution in response to a second stimulus.

The target protein may be expressed in host cells. The host cells may be any cells suitable for producing the target protein (e.g., antibody). Examples of host cells include Chinese hamster ovary (CHO) cells, *Escherichia co/i* cells, *Saccharomyces cerevisiae* cells, *Pichia pastoris* cells, and Human embryonic kidney (HEK) cells. In one embodiment, the host cells are CHO cells. In one embodiment, the target protein is expressed in *Escherichia* coll.

The conjugating step may comprise post-translational bacterial Sortase A mediated ligation.

In the preparation method, the first stimulus may consist of addition of the target protein to the first solution, the first solution may have a temperature of about 5-35° C., 10-35° C., 15-35° C., 5-25° C., 10-25° C. or 15-25° C., a salt concentration of about 1-1,000 mM, 5-500 mM, 10-500 mM, 50-500 mM, 50-200 mM, 100-200 mM, 50-150 mM or 100-150 mM and a pH of about pH 4-11, 5-10, 6-9 or 6-8, and the molar ratio of the affinity domain to the target protein in the first solution may be in the range of about 10:1-1:10, 6:1-1:6, 3:1-6:1 or 3:1-1:3. In one embodiment, the first stimulus consists of addition of the target protein to the first solution, the first solution has a temperature of about 15-25° C., a salt concentration of about 50-200 mM and a pH of about pH 6-9, and the molar ratio of the affinity domain to the target protein in the first solution is in the range of about 3:1-6:1. The first stimulus may further comprise a change to the first solution. The change to the first solution may be a change of temperature of the first solution, a change of salt concentration of the first solution, a change of pH of the first solution or a combination thereof. The first stimulus may exclude a change to temperature of the first solution. The change (e.g., elevation or reduction) of temperature of the first solution may be no more than about 50, 40, 30, 20, 10 or 5° C. The change (e.g., elevation or reduction) of salt concentration of the first solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the first solution may be no more than about 10, 9, 8, 7, 6, 5, 4, 3 or 2 pH units.

According to the preparation method, the second stimulus may be a change to the second solution. The change to the second solution may be a change of temperature of the second solution, a change of salt concentration of the second solution, a change of pH of the second solution or a combination thereof. The second stimulus may exclude a change to temperature of the solution. The change (e.g., elevation or reduction) of temperature of the second solution may be no more than about 50, 40, 30, 20, 10 or 5° C. The change (e.g., elevation or reduction) of salt concentration of the second solution may be no more than about 5, 4, 3, 2, 1, 0.5 or 0.1 M. The salt may have a cation selected from the group consisting of ammonium, potassium and sodium. The salt may have an anion selected from the group consisting of phosphate, sulfate, carboxylate and chloride. The change (e.g., elevation or reduction) of pH of the second solution may be no more than 10, 9, 8, 7, 6, 5, 4, 3 or 2 pH units. The second stimulus may be a change of temperature of the second solution to less than about 37, 35, 30, 25, 20, 15, 10, 5 or 4° C. In one embodiment, the second stimulus is a change of temperature of the second solution to less than about 25° C. The second stimulus may be a change of salt concentration of the second solution to less than about 1,000, 500, 200, 150 or 100 mM. In one embodiment, the second stimulus is a change of salt concentration of the second solution to less than about 200 mM. The second stimulus may be a change of pH of the second solution to less than about pH 7, 6, 5, 4, 3 or 2. In one embodiment, the second stimulus is a change of pH of the second solution to less than about pH 4.

The preparation method may further comprise solubilizing the nanoparticle into the solution. The solubilized nanoparticle may be recycled for affinity precipitation. The nanoparticle may be recycled for at least more about 10, 50, 100, 200 or 500 times.

The purification method of the present invention may be used for purification of monoclonal antibodies (mAbs) as an alternative for industrial production of mAbs to protein A chromatography. The benefits of the present method over protein A chromatography include reduced costs because no chemical conjugation or synthetic ligands is required and the antibodies may be produced in *E. coli*; ease of scale-up because the method may be easily adaptable to existing infrastructure (e.g., filtration, centrifugation); ease for mass transfer because the method eliminates pore diffusion and uses convection from mixing; high throughput (e.g., <1 hour purification; minimal buffer consumption); and equivalent yield and impurity clearance as Protein A chromatography. For purification of mAbs produced by host cells (e.g., *E. coli*), this method may provide more than 99.9% impurity clearance, more than 90% mAb yield, more than 95% monomer content, and/or more than 100 reuse cycles, and may be completed within 5, 10, 30, 60 or 120 minutes.

The functionalized nanoparticlein the present invention provides benefits over traditional Z-ELP precipitation methods, including minimized ELP transition temperature by conjugation of the Z-ELP to a scaffolding domain; enhanced crosslinking through multi-valent interactions; larger aggregate formation; little or no salt required for initial precipitation; elimination of heating step, for example, the entire process may be performed at ambient temperature; large, stable insoluble aggregates even at low temperature and salt; and adaptable to existing Protein A chromatography wash and elution conditions.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate.

Example 1. Enhanced Affinity Precipitation of Antibodies Using Functionalized Protein Nanoscaffolds Recent advancements in upstream therapeutic monoclonal antibody (mAb) production have posed significant challenges for platform downstream purification. Protein A chromatography has been identified as a potential bottleneck due to limitations in throughput, scale-up, and cost. This has generated increased interest in non-chromatographic capture technologies. Affinity precipitation is a promising alternative because it combines high specificity with multiple operational benefits. An environmentally responsive, recombinant elastin-like polypeptide (ELP) genetically fused to an antibody affinity domain (Z-domain) has been shown to make an ideal candidate for antibody purification. However, elevated temperature and salt concentrations necessary to induce aggregation can diminish product quality and operational efficiency. To minimize the requirement of these harsh conditions, the scale of ELP aggregation is enlarged via conjugation to a novel protein nanoscaffold. A Z domain-ELP fusion (Z-ELP) was covalently bound to a modified, 25 nm diameter E2 core from the pyruvate dehydrogenase enzyme complex using post-translational Sortase A mediated ligation (Z-ELP-E2). Z-ELP-E2 nanoparticles demonstrated superior aggregation properties compared to Z-ELP, requiring significantly lower salt concentrations to precipitate the complex out of solution. The functionalized nanoscaffold was shown to effectively bind, precipitate, and elute a polyclonal human IgG antibody with high recovery (>95%). This process was evaluated using a mock industrial mAb culture supernatant, and high yield and purity was obtained. Affinity precipitation using the Z-ELP-E2 nanoscaffold exhibited a significant improvement over the existing ELP-based system, and has the potential to be a cost-effective, easily scalable alternative to platform Protein A chromatography.

I. MATERIALS AND METHODS

Materials

*Escherichia coli* strain BLR(DE3) containing pET24(a) vectors encoding for Z-ELP[KV$_8$F-40]-LPETG and ELP[KV$_8$F-40]-LPETG were constructed and described previously (Sun et al., ACS Nano, 9(8): 8554-8561 (2015)). *E. coli* strain BL21(DE3) containing a pET11(a) vector encoding for GGG-E2(158) and another BL21(DE3) strain containing a pMR5 vector encoding for SrtA enzyme were constructed and described previously (Chen et al., ACS Nano, 9(8): 8554-8561 (2015)). Human polyclonal IgG and FITC conjugated human IgG were purchased from Sigma-Aldrich (St. Louis, Mo.). Bacto tryptone and yeast extract were purchased from BD Biosciences (Franklin Lakes, N.J.). Glycerol, kanamycin, ampicillin, isopropyl-β-D-thiogalactoside (IPTG), calcium chloride and sodium chloride were purchased from Fisher Scientific (Pittsburgh, Pa.). Sodium hydroxide, potassium mono and dibasic phosphate, sodium phosphate dibasic, bovine serum albumin (BSA), L-arginine, tris base, and ammonium sulfate were purchased from Sigma-Aldrich (St. Louis, Mo.). 100 kDa Vivaspin 20 columns were purchased from Sartorius Stedim (Gottingen, Germany). All statistical analyses were performed in Minitab 17.

Protein Expression and Purification

Z-ELP[KV$_8$F-40]-LPETG and ELP[KV$_8$F-40]-LPETG were expressed in BLR(DE3) *E. coli* cells grown in Terrific Broth medium (TB) with 50 μg/mL kanamycin at 37° C. and 250 rpm for 24 hours with leaky expression. SrtA was expressed in BL21(DE3) *E. coli* cells grown in Luria-Bertani Medium (LB) with 50 μg/mL kanamycin at 37° C. and 250 rpm until an OD600 of 1.0, where the culture was induced with 1 mM IPTG and subsequently incubated at 37° C. for 4 hours. GGG-E2 was expressed in BL21(DE3) *E.* coli cells grown in LB with 100 μg/mL ampicillin at 37° C. and 250 rpm until an OD600 of 0.5, where the culture was induced with 0.2 mM IPTG and subsequently incubated at 20° C. for 20 hours. After protein expression, all cultures were harvested by centrifugation at 4,000 g for 15 min at 4° C. and resuspended in a tris buffer (50 mM Tris, 150 mM NaCl, pH 8.0). Cells were lysed using a Fisher Sonicator (Pittsburgh, Pa.) using 5 s pulse on and 10 s pulse off for 10 min over ice. Soluble lysate was separated by centrifugation at 15,000 g for 20 min at 4° C. ELPs were purified using three rounds of ITC as described previously (Meyer & Chilkoti, Nat Biotechnol 17(11):4 (1999)) using 0.5 M ammonium sulfate for precipitation and were resuspended in the tris buffer. Molar concentration of purified ELP was determined by measuring absorbance at 280 nm on a Shimadzhu UV-1800 spectrophotometer (Kyoto, Japan). The expressed GGG-E2 scaffold is thermo-stable and was purified by incubating at 70° C. for 10 min to precipitate contaminant proteins. The soluble fraction was separated by centrifugation at 15,000 g for 15 min. Total protein concentration of purified GGG-E2 and soluble SrtA lysate were measured by Bradford protein assay purchased from Bio-Rad (Hercules, Calif.) using BSA as a standard. Protein expression was confirmed by Coomassie stained, 10% acrylamide SDS-PAGE using a Bio-Rad Mini-PROTEAN electrophoresis system (Hercules, Calif.). Protein purity was estimated using densitometry analysis of the SDS-PAGE gel using Thermo MyImage software (Waltham, Mass.).

Sortase A Mediated Ligation of ELP to the E2 Scaffold

Ligation of ELP-LPETG or Z-ELP-LPETG to the E2 scaffold was catalyzed by the SrtA enzyme following SrtA-mediated ligation methods described previously (Levary et al., Bioconjugate Chem. 18:469-476 (2011)). 50 μm Z-ELP or ELP, 10 μm E2, and 10 μm SrtA were added to a reaction buffer consisting of 50 mM tris, 150 mM sodium chloride, 6 mM calcium chloride, pH 8.0 in a centrifuge tube. The reaction mixture was incubated at 37° C. for 4 hr to allow for SrtA to catalyze the formation of a covalent bond between the C- and N-terminal recognition motifs. The ligation product was purified using one round of inverse transition cycling using 1 M ammonium sulfate and was resuspended in phosphate buffered saline (PBS; 137 mM NaCl, 2.7 mM KCl, 10 mM $Na_2HPO_4$, 2 mM $KH_2PO_4$, pH 7.4). The excess, unreacted ELP was removed by 100 kDa diafiltration into PBS using Sartorius Vivaspin 20 spin columns. A second round of inverse transition cycling was used to concentrate the purified ligation product. The resulting Z-ELP-E2 or ELP-E2 nanoparticle was confirmed by Coomassie stained 10% acrylamide SDS-PAGE and ELP ligation density was estimated using densitometry analysis. FIG. 1 summarizes the process for constructing the ELP-E2 nanoparticles using SrtA ligation shown with each step's corresponding SDS-PAGE gel image. The ligation products were characterized by dynamic light scattering (DLS) using a Malvern Zetasizer Nano (Malvern, United Kingdom) and by transmission electron microscopy (TEM) with a Zeiss Libra 120 Electron Microscope (Oberkochen, Germany) using 2% uranyl acetate staining on a carbon coated grid from Electron Microscopy Sciences (Hatfield, Pa.).

Z-ELP-E2 and Z-ELP Aggregation Comparison

A comparison of Z-ELP-E2 and Z-ELP transition profiles and $T_t$s was evaluated using UV spectroscopy over a temperature gradient. Equal concentrations of free Z-ELP and ligated Z-ELP to the E2 scaffold surface were prepared at 4° C. in PBS with various ammonium sulfate concentrations (0, 0.1, 0.2, 0.3, 0.5 M) and were incubated at 4° C. for 30 min. The aggregation transition curves of the samples were evaluated using a Shimadzhu UV-1800 spectrophotometer measuring the absorbance at 350 nm every 0.5 degrees from 4-65° C. at a ramp rate of 0.5 degree per min with a 10 second equilibration before each measurement. Three separate measurements were performed for each condition and the $T_t$ was calculated by evaluating the maximum slope of the transition curve. Two-sample t-tests were employed to determine the statistical significance of the hypothesized difference of Tts between free Z-ELP and Z-ELP ligated to the E2 scaffold.

A comparison of aggregation kinetics after IgG binding and aggregate size after precipitation was evaluated using dynamic light scattering. The hydrodynamic diameter was measured at 25° C. using a Malvern Zetasizer Nano with a 4 mW He Ne gas laser at 632.8 nm and a 175° scattering angle. For each data point, three measurements were taken each consisting of 3 runs of 10 s and the correlation function was analyzed by the Protein Analysis algorithm provided by the Malvern software. Equal concentrations of both free Z-ELP and Z-ELP ligated to E2 scaffolds were prepared with a human polyclonal IgG at a 5:1 ratio in PBS at room temperature. Samples containing free ELP (with no Z-domain) and ELP ligated to E2 cage were also prepared with IgG at a 5:1 ratio as a control. Immediately after preparing each sample, the hydrodynamic radius was measured and then measured again at approximately 10 min intervals over the next 90 minutes while maintaining all samples at room temperature. After the incubation period, the ammonium sulfate concentration was increased step-wise from 0.1 to 0.5 M using a 3 M stock solution. After each addition, the solution was incubated at room temperature for 30 minutes before measuring the hydrodynamic radius.

A comparison of aggregate size was further investigated with fluorescent microscopy using a Zeiss Observer Z1 inverted microscope (Oberkochen, Germany) equipped with a filter set consisting of an ET470/40x exciter, ET525/50 m emitter, and a T495Ipxt beam splitter from Chroma Technology (Bellows Falls, Vt.). Images were acquired using a Zeiss AxioCam MRm camera and analyzed using Zeiss AxioVision microscopy software (Oberkochen, Germany). FITC-conjugated human IgG was incubated at a 5:1 ratio with equal concentrations of both free and ligated Z-ELP. After incubation at room temperature for one hour, 8 μL of each sample was added to a Fisher microscope slide (Pittsburgh, Pa.) with a coverslip, and a fluorescent microscopy image was taken. The samples were then adjusted to 0.5 M ammonium sulfate, incubated for 15 min at room temperature, and imaged again.

Turbidity was measured by absorbance at 350 nm using a Synergy H4 microplate reader purchased from Biotek (Winooski, Vt.). Samples were prepared with equal concentrations of free and ligated Z-ELP and were mixed with human polyclonal IgG at a 5:1 molar ratio in PBS and incubated at 23° C. for two hours in microcentrifuge tubes. After the initial incubation, samples were adjusted to 0.5M ammonium sulfate and pelleted by centrifugation at 15,000 g. Samples were resuspended back in PBS and incubated for 1 hour and 3 days at 4° C. with mixing. After incubation, samples were precipitated with 0.5M ammonium sulfate and pelleted by centrifugation at 15,000 g. Samples were resuspended in the elution buffer and incubated at 23° C. for 15 min. Turbidity was measured immediately after each sample was taken. All experimental samples were run in triplicate.

Antibody Affinity Precipitation

Figure 9:
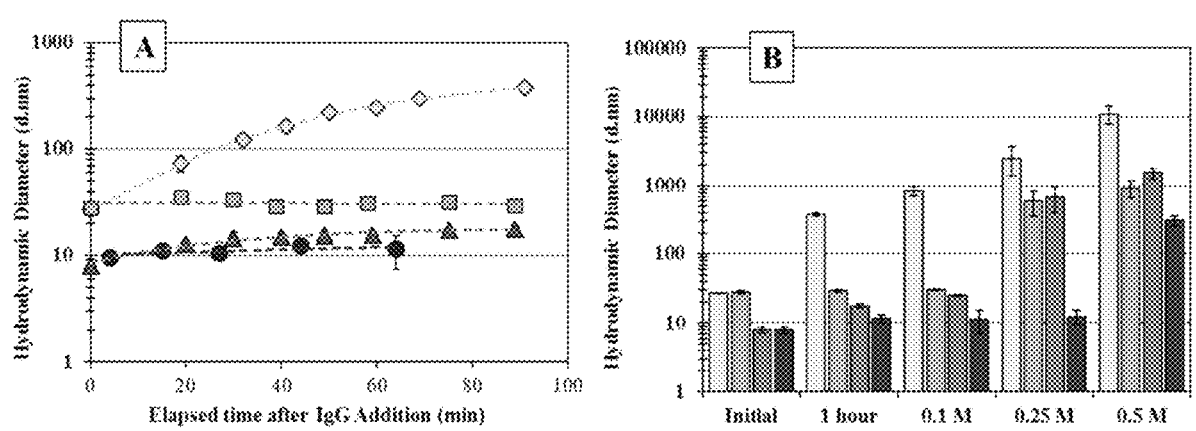
FIG. 9 shows aggregation size comparison for equal concentrations of ligated and free Z-ELP after IgG addition. A) Kinetics of IgG binding and aggregation at 25° C. in PBS. Light grey diamond: Z-ELP-E2 nanoparticle, medium light grey square: ELP-E2 nanoparticle, medium dark grey triangle: Z-ELP, dark grey circle: ELP. Values represent an average of three measurements. Error bars represent 95% confidence intervals (not visible). First time point is measured immediately after adding IgG to the mixture. B) Aggregate size analysis of samples after IgG addition and after adjusting solution to increasing concentration of ammonium sulfate salt. Light grey bars: Z-ELP-E2 nanoparticle, medium light grey bars: ELP-E2 nanoparticle, medium dark grey bars: Z-ELP, dark grey bars: ELP. Initial values measured immediately after adding IgG to the mixture. All measurements taken at 25° C. Values are an average of three measurements. Error bars represent 95% confidence intervals.
Figure 14:
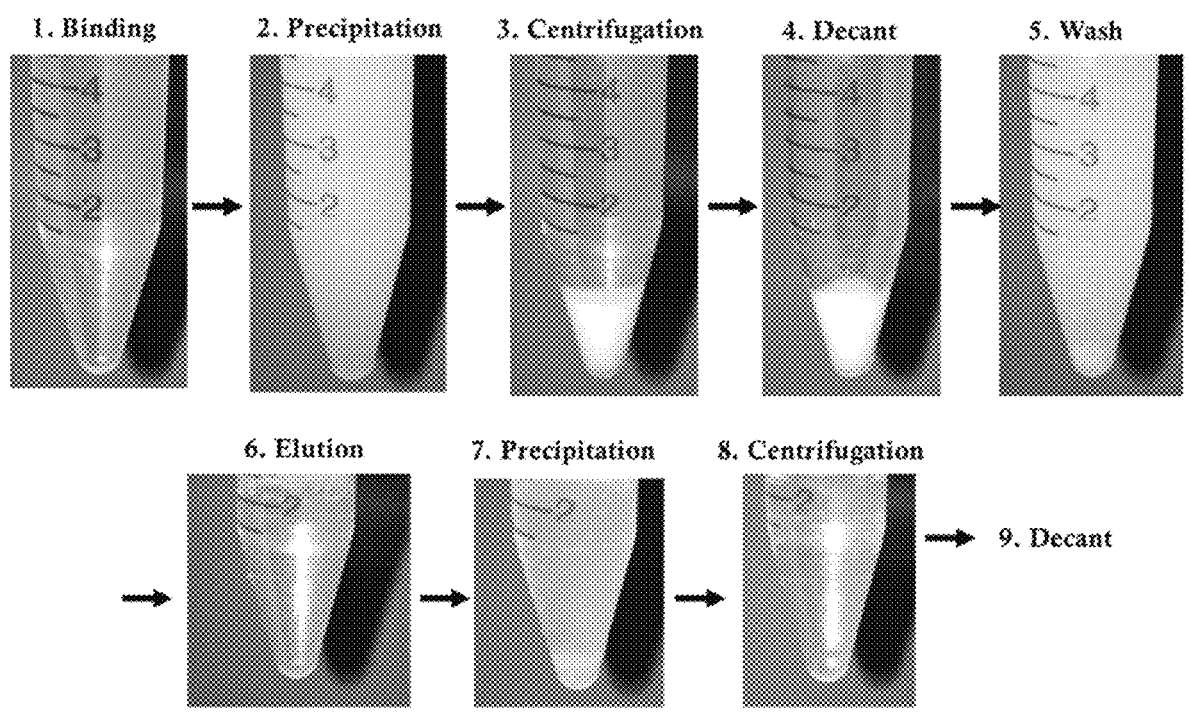
FIG. 14 shows an example IgG purification process steps with pictures.
Figure 15:
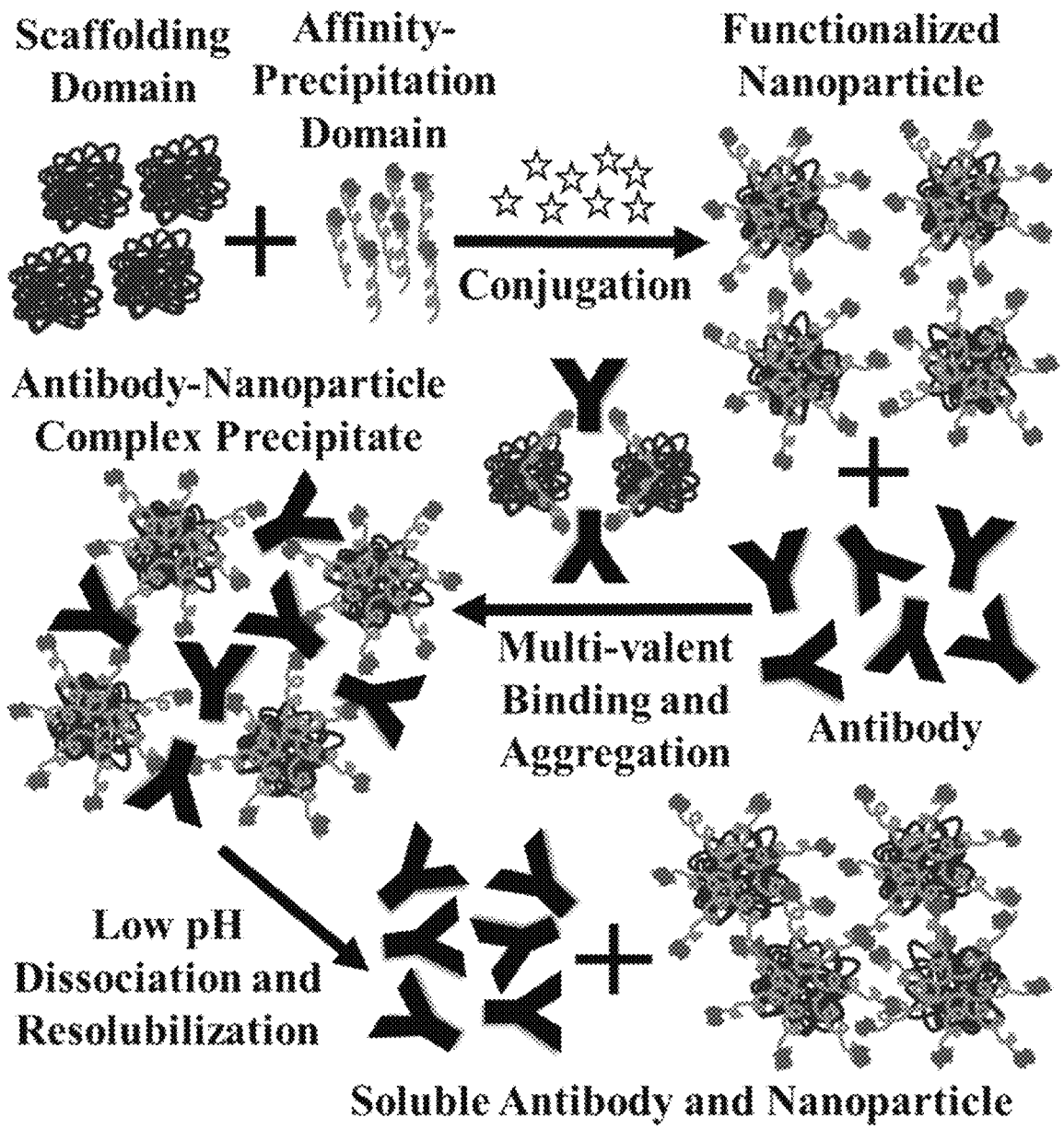
FIG. 15 shows one embodiment of the invention.

IgG affinity precipitation yield was compared between free Z-ELP and Z-ELP ligated to the E2 scaffold at different salt concentrations. Affinity precipitation consists of three steps: binding, precipitation, and elution. First, equal concentrations of free Z-ELP and ELP, and ligated Z-ELP-E2 and ELP-E2 cages were mixed with human polyclonal IgG at a 5:1 molar ratio in PBS and incubated at room temperature for one hour in microcentrifuge tubes. ELP and ELP-E2 do not contain a Z-domain and were used as controls. Second, the complex was precipitated using various concentrations of ammonium sulfate (0.1, 0.25, and 0.5 M) and incubated at room temperature for 10 minutes. The solution was centrifuged for 10 min at 15,000 g at 25° C. to pellet the precipitate. Third, the supernatant was removed and the pellet was resuspended in elution buffer (0.5 M arginine, pH 3.7) and incubated for one hour at 4° C. A second precipitation was performed using 1 M ammonium sulfate for all arms to precipitate the ELP. Upon another centrifugation, the IgG was separated in the supernatant from the ELP in the pellet. FIG. 9 summarizes the affinity precipitation procedure and FIG. 14 depicts images for each step. Bradford assay was used to quantify IgG recoveries using a standard curve prepared with known IgG concentrations. IgG recovery was calculated by the IgG mass in the supernatant after elution divided by the initial IgG mass added. SEC was used to quantify IgG aggregate content of the eluted IgG. All experimental conditions were run in triplicate. To evaluate the purification of a mock cell culture, non-secreting Chinese hamster ovary (CHO) cells grown in SFM4CHO media from GE Healthcare (Little Chalfont, United Kingdom) were collected on day 14 post inoculation, and lysed by sonicating on ice for 5 pulses of 30 Amps for 5 s each. The soluble lysate was collected by centrifugation. Z-ELP-E2 cages and model IgG were added directly to the lysate at a 5:1 molar ratio. The affinity precipitation process was performed as described above using 0.5 M ammonium sulfate for precipitation. Bradford assay was used to determine IgG yield and purity was determined by SDS-PAGE.

Size Exclusion Chromatography

Size exclusion chromatography (SEC) was used to analyze IgG aggregate content of the model human IgG polyclonal antibody initially and post elution from the nanoparticles. A TSKgel G3000SW XL SEC column (7.8 mm×30 cm, 250 Å pore) from TOSOH (Tokyo, Japan) was utilized on an Agilent 1100 HPLC from Hewlet Packard (Palo Alto, Calif.). A mobile phase consisting of 0.5% (v/v) phosphoric acid and 50 mM sodium chloride, pH 3.5 was used at a flowrate of 0.75 µL/min at 25° C. and effluents were monitored by absorbance at 280 nm. 75 µL sample was injected per run and each sample was run in triplicate. All samples were prepared at the same IgG concentration measured by Bradford assay with a known standard curve. The initial sample was prepared using pure IgG diluted in elution buffer with 1 M ammonium sulfate.

II. RESULTS AND DISCUSSION

Production and Characterization of the Functionalized Nanoscaffolds

Figure 2:
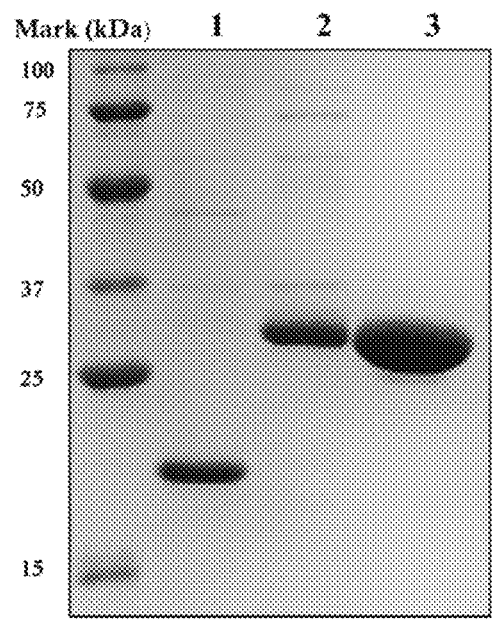
FIG. 2 shows Coomassie stained, reducing 10% acrylamide SDS-PAGE of the SrtA ligation reactants at target concentration ratios. Lane 1: 10 μM SrtA soluble lysate (17 kDa). Lane 2: 10 μM E2 purified by 70° C. heating (29 kDa). Lane 3: 50 μM Z-ELP purified by two ITC cycles (28 kDa).
Figure 3:
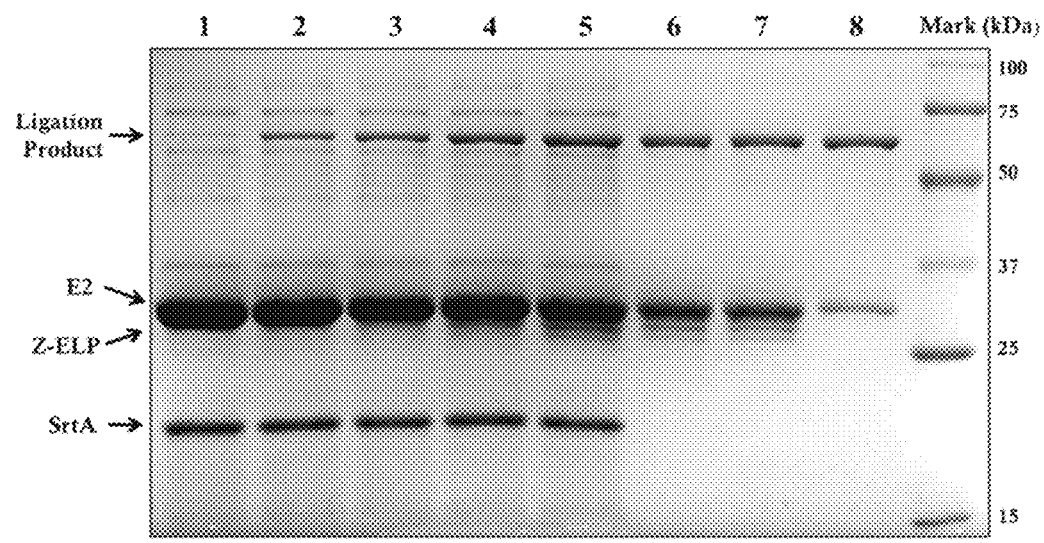
FIG. 3 shows Coomassie stained, reducing 10% acrylamide SDS-PAGE of the ligation reaction time-course and Z-ELP-E2 nanoparticle purification. Sample loading normalized by volumetric concentration. Reaction quenched with 25 mM EDTA. Lane 1: Initial mixture of ligation reactants in reaction buffer. Lane 2: 30 min reaction. Lane 3: 1 hr reaction. Lane 4: 2.5 hr reaction. Lane 5: 5 hr reaction. Lane 6: Ligation product purification by ITC cycle 1. Lane 7: ITC cycle 2. Lane 8: 100 kDa filtration retentate.

To construct the nanoscaffold using SrtA ligation, purified E2 and Z-ELP were mixed with SrtA lysate at optimal target concentrations in a reaction buffer containing $Ca^{2+}$ ions (FIG. 2). An example of an optimized reaction was characterized by SDS-PAGE analysis (FIG. 3). The ligation product band (55 kDa), consisting of covalently bound Z-ELP to one of the E2 subunits, intensified over time (lanes 2-5). The product was purified by two rounds of ELP ITC, removing SrtA and all other lysate impurities (lane 6-7). However, residual, unreacted Z-ELP was co-precipitated, so a filtration step was implemented to isolate the purified nanoparticles. Upon 100 kDa diafiltration into PBS, the remaining unreacted Z-ELP sieved through the filter, while the nanoparticle remained in the retentate (lane 8). This procedure offers a facile, non-chromatographic purification of functionalized E2 scaffolds from *E. coli* lysate impurities.

Figure 4:
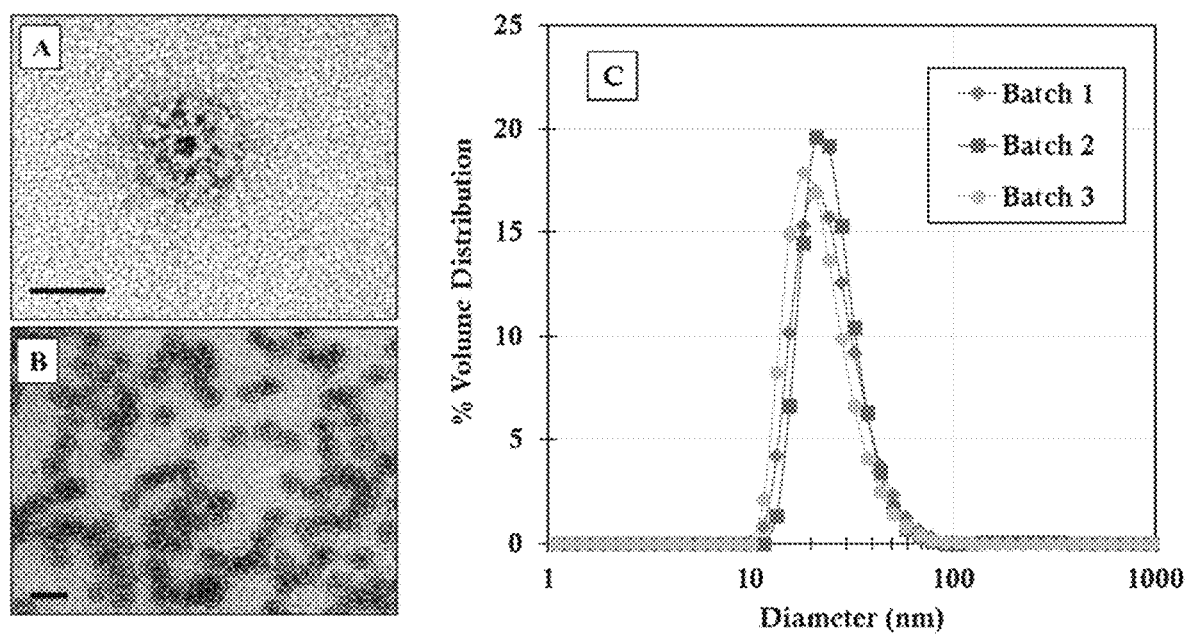
FIG. 4 shows Z-ELP-E2 nanoparticle size characterization by TEM and DLS. A) TEM image of a single Z-ELP-E2 nanoparticle. Scale bar represents 20 nm. B) TEM image of a solution of many Z-ELP-E2 nanocages. Scale bar represents 50 nm. C) DLS % volume particle distribution for purified solutions of 2 mg/mL nanoparticle. The three batches represent nanoparticle produced using ligation reactant proteins expressed from different cultures.

After ligation and purification, TEM and DLS were utilized to confirm the nanoparticle structure and size. TEM images of a single nanoparticle (FIG. 4A) and mixture of nanoparticles (FIG. 4B) depicts the expected dodecahedron structure and size consistent with previous analysis (Zhou, Liao et al., J Biol Chem 276(15):21704-21713 (2001)). FIG. 4C shows DLS volume distributions for three nanoparticle ligation products produced from different cultures of reactant proteins. The measured samples had a polydispersity<0.3 and an average hydrodynamic radius of 34.5±2.8 nm. These results indicate that a highly pure, monodisperse solution of self-assembled Z-ELP-E2 nanoparticles can be consistently produced using the indicated procedures.

Figure 5:
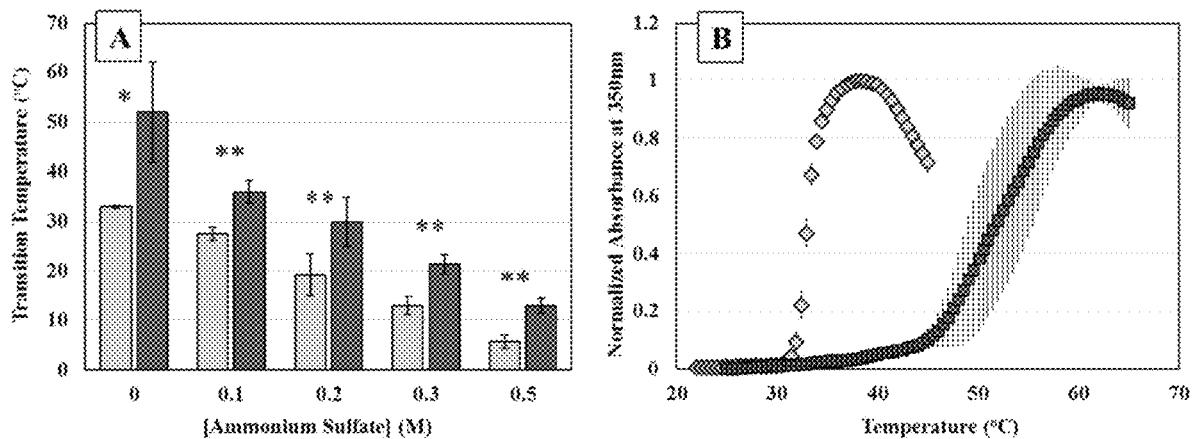
FIG. 5 shows $T_t$ comparison between equal concentrations of ligated and free Z-ELP. $T_t$ is defined by the maximum slope of the absorbance curve at 350 nm over a temperature gradient. A) $T_t$ of the nanocage and free Z-ELP with different concentrations of ammonium sulfate. Light grey bars: Z-ELP-E2 nanoparticles, dark grey bars: Z-ELP. Error bars represent 95% confidence intervals of three separate experiments. *=p-value<0.01 difference in $T_t>10°$ C., **=p-value<0.01 difference in $T_t>5°$ C. B) Normalized, background corrected absorbance curve at 350 nm for the nanoparticle (light grey diamond) and free Z-ELP (dark grey square) in PBS. Error bars represent one standard deviation of three separate experiments.

After isolating the purified nanoparticles, the $T_t$, defined as the temperature at which 50% of protein has precipitated, was found to be significantly lower than equal concentrations of free Z-ELP in solution. The $T_t$ was measured for ligated Z-ELP and free Z-ELP in PBS with different concentrations of ammonium sulfate (FIG. 5A). For the samples prepared with ammonium sulfate (0.1-0.5 M), the nanoparticle exhibited a >5° C. lower transition than free Z-ELP (p<0.01). Without any added salt (PBS), the difference in $T_t$ was >10° C. (p<0.01). Minimizing the $T_t$ of the nanoparticle is ideal for an antibody affinity precipitation process because this, in turn, minimizes the amount of salt required for precipitation at a given temperature. Furthermore, the nanoparticle transition region occurs within five degrees and is marked by a sharp increase in turbidity, whereas the transition for free Z-ELP occurs over 15 degrees with a much smaller slope (FIG. 5B). This is important because for affinity precipitation, it is important to operate at the peak temperature at which 100% of the ELP has precipitated. The difference in peaks between the two samples was greater than 20° C., further magnifying the benefit of ELP ligation to a nanoscaffold.

Antibody Affinity Precipitation with Protein Nanoparticles

Figure 6:
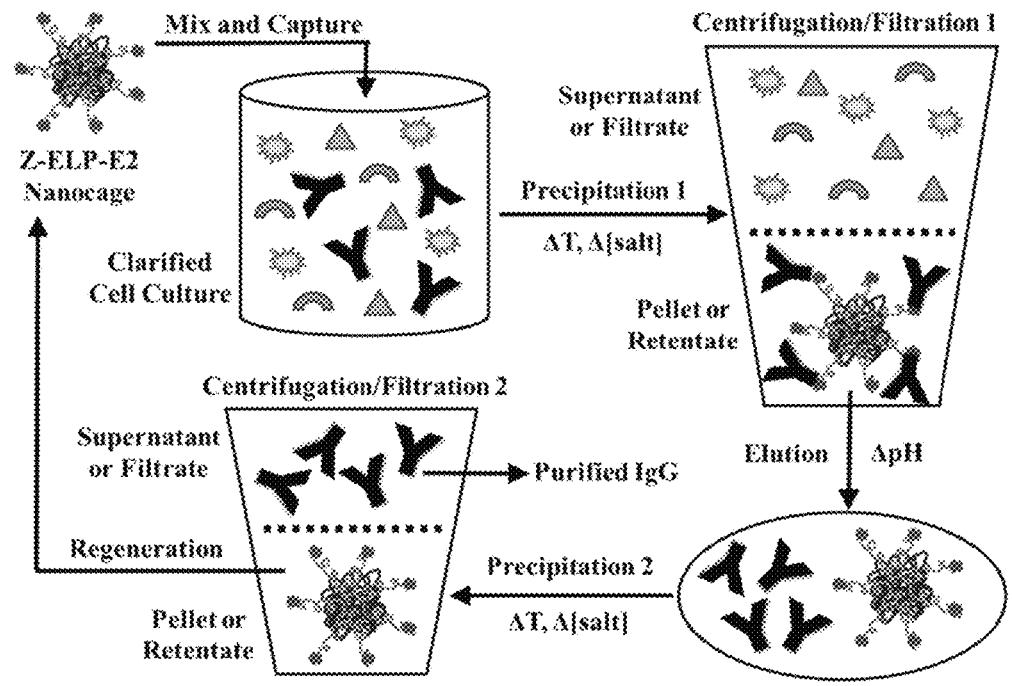
FIG. 6 shows an example IgG affinity precipitation process. The Z-ELP-E2 nanoparticle is added to clarified IgG cell culture containing the target antibody as well as unwanted host cell and media impurities. After allowing sufficient time for the IgG to bind to the Z-domain, the salt concentration and/or temperature is increased to precipitate the IgG-Z-ELP-E2 complex. The complex is separated from culture impurities via either centrifugation or filtration. Antibodies are then eluted from the Z-domain by lowering the pH of the solution. Upon a second precipitation, the purified antibodies are separated from the nanoparticles. The nanoparticles are regenerated and recycled for future use.

The proposed antibody affinity precipitation procedure (FIG. 6) can be adapted to common, existing manufacturing processes without the need for any specialized equipment. The application and consideration of affinity precipitation at large scale has been reviewed previously (Hilbrig and Freitag, Biotechnol Prog 26(5):1400-1410 (2003)). To demonstrate the benefit of lower $T_t$ on IgG recovery, the affinity precipitation process was performed using equal concentrations of ligated Z-ELP and free ELP and a purified model polyclonal human IgG. After Z-domain to binding to the IgG Fc-region, the complex was precipitated with varying concentrations of ammonium sulfate at 25° C. followed by elution with low pH. Control samples consisting of IgG with ELP-E2 and free ELP (no Z-domain) were employed to test for non-specific binding.

Figure 7:
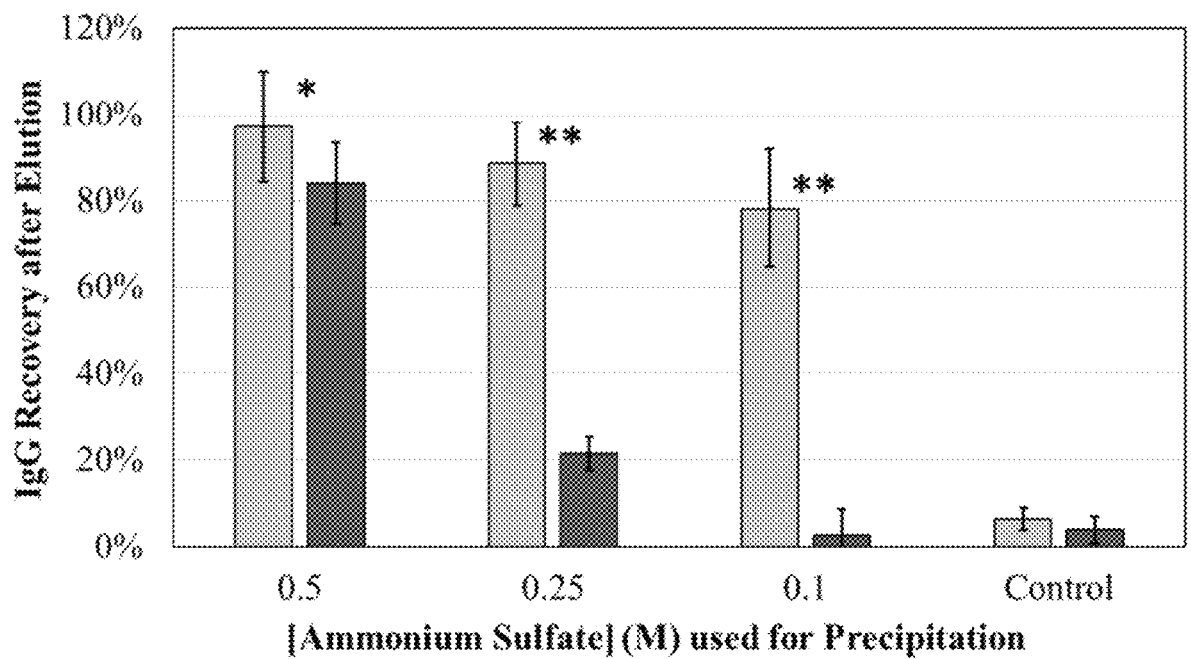
FIG. 7 shows affinity precipitation IgG recovery comparison for equal concentrations of ligated and free Z-ELP. Light grey bars: Z-ELP-E2 nanoparticles, dark grey bars: Z-ELP. Human polyclonal IgG was purified using the process shown in FIG. 4 using the indicated concentration of ammonium sulfate. The control values represent the ELP-E2 nanoparticle control and ELP control (with no Z-domain) using 0.5M ammonium sulfate for precipitation. IgG % recovery was quantified by the final mass IgG in the elution divided by the initial mass of IgG stock added as measured by Bradford assay using a standard curve with known IgG concentrations. Data values represent an average of three experiments. Uncertainty was propagated through recovery calculations. Error bars represent 95% confidence intervals. *p-value=0.023, **p-value<0.001.
Figure 8:
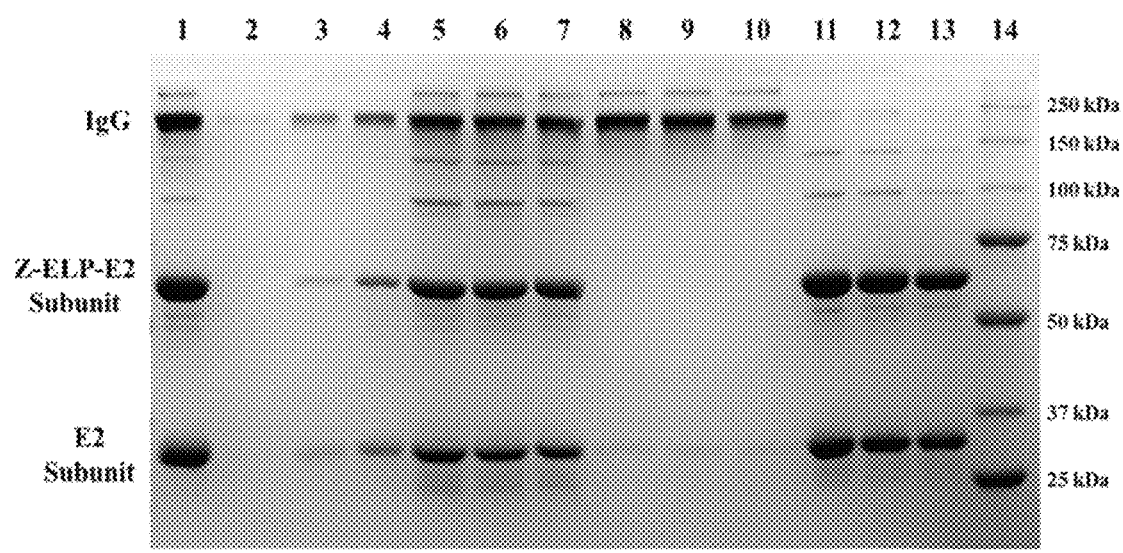
FIG. 8 shows Coomassie stained 8% acrylamide non-reducing SDS-PAGE gel of IgG purification using Z-ELP-E2 nanoparticles and different concentration of ammonium sulfate for precipitation. Lane 1=Initial mixture of IgG and Z-ELP-E2. Lane 2, 5, 8, and 11 use precipitation with 0.5M ammonium sulfate. Lane 3, 6, 9, and 12 use precipitation with 0.25M ammonium sulfate. Lane 4, 7, 10, and 13 use precipitation with 0.1M ammonium sulfate. Lanes 2-4 represent precipitation 1 supernatant. Lanes 5-7 represent precipitation 1 pellet. Lanes 8-10 represent precipitation 2 supernatant. Lanes 11-13 represent pellet 2. Lane 14 is the molecular weight marker.
Figure 13:
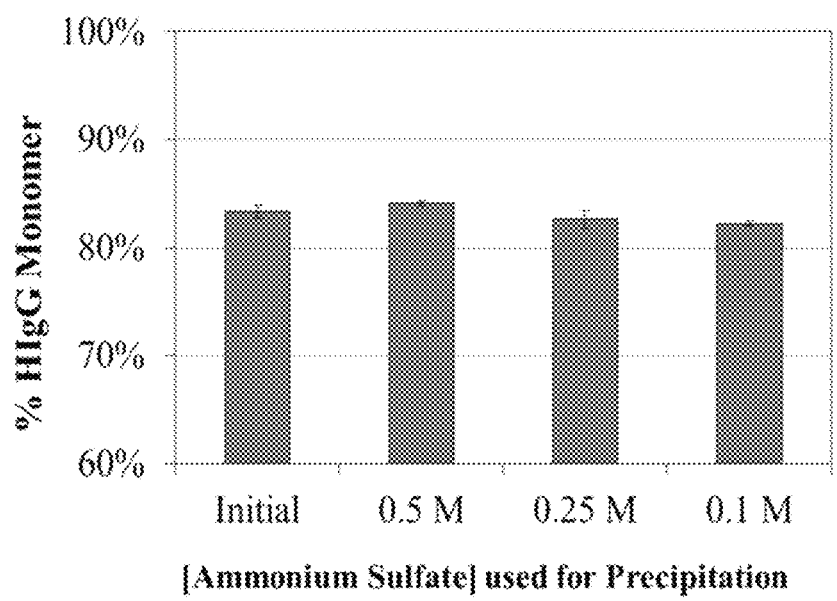
FIG. 13 shows IgG aggregate content after elution from the Z-ELP-E2 nanoparticle using different salt concentrations for precipitation quantified by SEC. Initial sample represents pure IgG diluted in elution buffer with 1 M ammonium sulfate. Error bars represent the 95% confidence interval of the three replicates for each sample.

As expected, precipitation with the nanoparticle greatly improved the antibody yields under the same operational conditions (FIG. 7). Precipitation with 0.5 M ammonium sulfate using the nanoparticle resulted in >95% recovery, while free Z-ELP, under the same conditions, had significantly lower yield (p=0.023). For both ligated and free Z-ELP, lower salt concentrations used for precipitation unsurprisingly resulted in lower yield. However, IgG recovery using free Z-ELP dropped sharply below 0.5 M ammonium sulfate, whereas nanoparticle recovery with 0.1 M salt only decreased to about 80%. Furthermore, approximately equal IgG yield was obtained while using five-fold less salt than Z-ELP precipitation at 0.5 M. An SDS-PAGE analysis of the nanoparticle precipitation process confirms the yield loss occurs in the initial supernatant (FIG. 8, lanes 2-4). These results corroborate with the $T_t$ data (FIG. 5A). The Z-ELP $T_t$ for ammonium sulfate concentrations<0.3 M were significantly higher than room temperature (25° C.). Therefore, the majority of IgG bound to Z-ELP was not precipitated because the precipitation conditions were below the ELP $T_t$. In addition, the control precipitation samples had very low recovery indicating negligible non-specific interaction between the antibody and the ELP or E2 scaffold. Lastly, SEC was used to monitor aggregate content of the eluted antibodies from the nanoparticle (FIG. 13). The aggregate content was equivalent for the initial and eluted IgG, indicating minimal impact of the affinity precipitation process on antibody product quality. This analysis confirms that significantly lower salt concentrations can be used to precipitate antibodies using the Z-ELP-E2 nanoparticles compared to free Z-ELP.

Characterization of IgG-Nanoparticle Complex and Aggregation

Interestingly, the IgG-nanoparticle complex with 0.1 M ammonium sulfate was sufficient to precipitate and elute over 80% of the added IgG at 23° C. This result cannot be explained simply by the improved transition property as the nanoparticle $T_t$ is 30° C. in the presence of 0.1M salt without IgG. It has been shown that ELP domain dimerization can be used to lower the $T_t$ values by increasing the local aggregate size. Because one IgG molecule can bind two Z domains, a similar dimerization mechanism likely exists. The addition of IgG can potentially act as a crosslinking agent through multi-valent binding, resulting in network formation between individual Z-ELP-E2 nanoparticles. To verify the hypothesis, the size of bound IgG aggregates was characterized by DLS and fluorescent microscopy. The initial IgG binding kinetics were monitored by measuring the hydrodynamic diameter over time (FIG. 9A). Samples consisting of Z-ELP-E2 nanoparticle, ELP-E2 nanoparticle (with no Z-domain), Z-ELP, and ELP (with no Z-domain) were prepared at equal ELP concentrations at room temperature in PBS. The initial sizes of the nanoparticle samples were ~30 nm as expected, and the size of free Z-ELP samples were ~8 nm, roughly the size of the model polyclonal antibody.

An order of magnitude increase in the particle size of Z-ELP-E2 upon the addition of IgG, while, no change in particle size was observed for the control ELP-E2 nanoparticles. Only a small increase in particle size was detected for Z-ELP from 8 to 18 nm, consistent with the formation of smaller localized dimers by IgG crosslinking. The control samples without a Z-domain remained the same size, providing evidence of minimal non-specific interactions. These results indicate a major aggregation event occurs after mixing IgG with the nanoparticle at room temperature in PBS. The hydrodynamic diameter was measured after 1 hour at room temperature and sequential additions of ammonium sulfate (FIG. 9B). As expected, the Z-ELP-E2 nanoparticle aggregate size increased with increased salt concentration. Z-ELP forms order of magnitude smaller aggregates at all salt concentrations tested compared to the nanoparticle.

Figure 10:
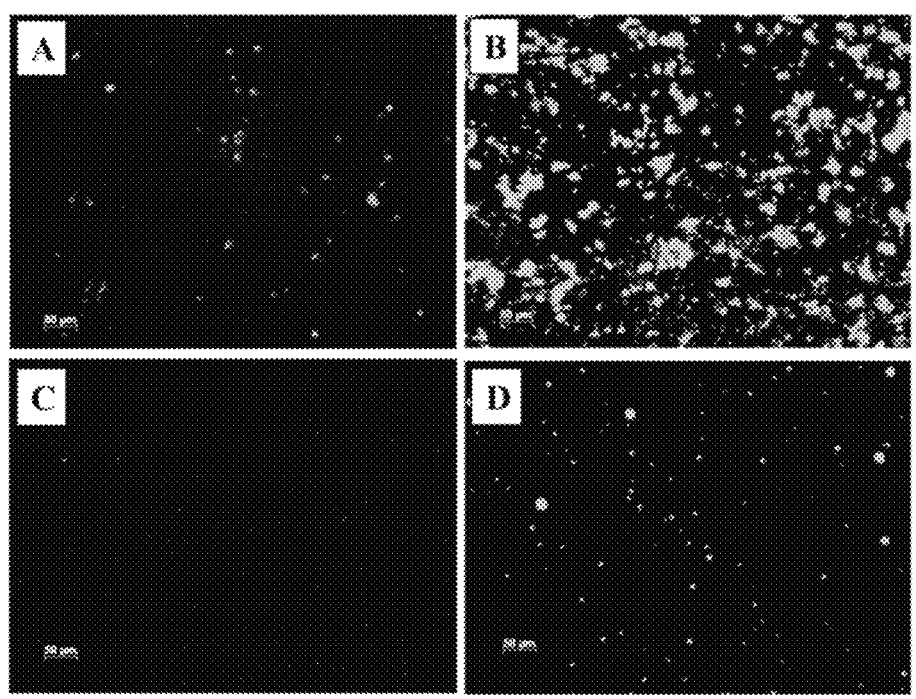
FIG. 10 shows comparison of aggregate sizes after IgG binding and precipitation using fluorescence microscopy of FITC-conjugated IgG. Scale bars=50 μm estimate. A) Solution of FITC-IgG and Z-ELP-E2 nanoparticle after 1 hr incubation in PBS at room temperature. B) Same solution in A) after adjusting to 0.5 M ammonium sulfate and incubated at room temperature for 10 min. C) Solution of equal concentrations of FITC-IgG and free Z-ELP as in A) after 1 hr incubation in PBS at room temperature. D) Same solution in C) after adjusting to 0.5 M ammonium sulfate.

Network formation by IgG crosslinking was further confirmed fluorescent microscopy of fluorescently-labeled IgGs (FIG. 10). Ligated and free Z-ELP were prepared with FITC-IgG and the solution was imaged after 1 hour at room temperature in PBS (FIG. 10A and FIG. 10C). Large particles were observed only for the IgG-nanoparticle complex (FIG. 10A). After adjusting to 0.5 M ammonium sulfate, the IgG-nanoparticle complex aggregates were 10-100 micron in size (FIG. 10B) and were 10-100 fold larger than those found in the IgG-Z-ELP sample (FIG. 10D). The spontaneous crosslinking of IgG-Z-ELP-E2 into large aggregates is highly advantageous for antibody purification because it allows for the selective precipitation of mAbs with substantially lower salt concentration and can eliminate the need for a heating step.

Figure 11:
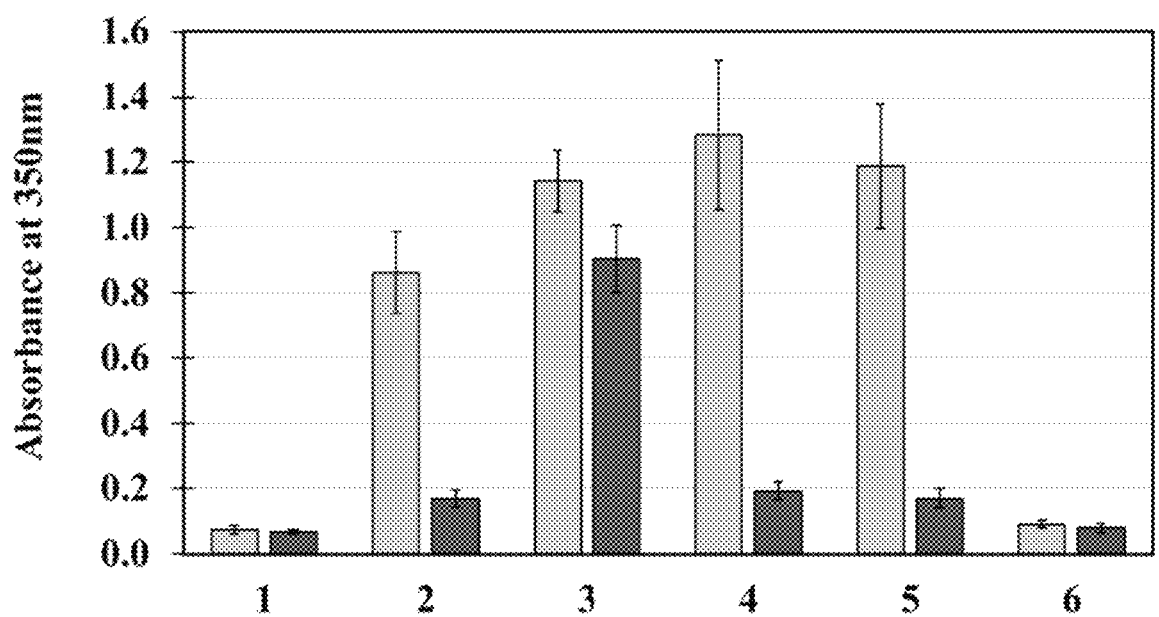
FIG. 11 Bound IgG to the Z-ELP-E2 nanoparticle complex remained insoluble until elution. Equal concentrations of ligated and free Z-ELP were mixed with polyclonal HIgG prepared in PBS at 23° C. Aggregation was reflected by measuring the turbidity at 350 nm. Error bars represent 95% confidence intervals of three experiments. Light grey bars: Z-ELP-E2 nanoparticle. Dark grey bars: Z-ELP (1) Initial sample before IgG addition. (2) 2 h incubation at 23° C. (3) Adjusted to 0.5 M ammonium sulfate. (4) Centrifuged and resuspended back into PBS and incubated at 4° C. for 1 h. (5) Incubated at 4° C. for 3 days. (6) Precipitated again and resuspended in elution buffer pH 3.7 and incubated at 23° C. for 15 min.

Conventional ELP inverse transition cycling involves the reversible resolubilization at low salt and temperature after precipitation, a property Z-ELP maintains when bound to IgG as reflected by the turbidity measurement. However, because of the substantial crosslinking, IgG bound Z-ELP-E2 precipitates remained insoluble even after 3 days in PBS at 4° C. (FIG. 11, lane 4-5). This irreversible phase transition enables the repeated washing in low salt buffers at low temperatures without affecting IgG recovery. This property also allows for extended storage of the IgG-Z-ELP-E2 complex in the precipitated state. Complete resolubilization was only observed after eluting the bound IgG at pH 3.7 (FIG. 11, lane 6), indicating the feasibility to achieve IgG purification by isothermal switching of phase separation.

Purification of a Challenging Mock mAb Culture.

Figure 12:
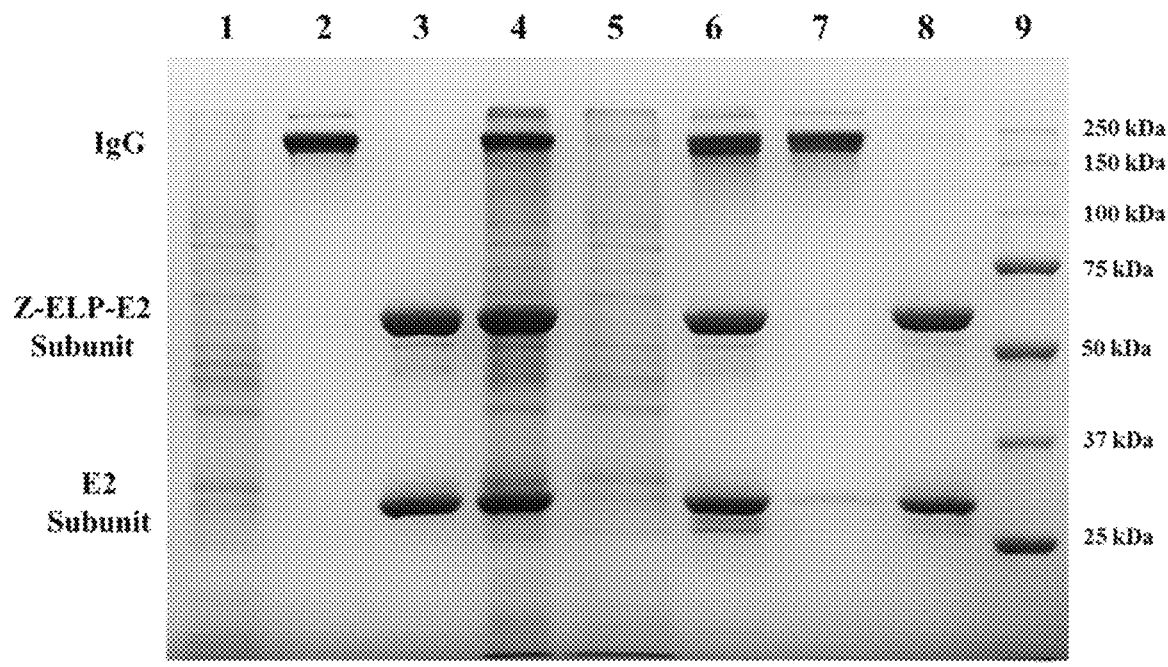
FIG. 12 shows Coomassie stained 8% acrylamide non-reducing SDS-PAGE gel of the affinity precipitation of IgG from a mock mAb culture supernatant using CHO cell lysate. 0.5M ammonium sulfate at 25° C. used for precipitation. Lane 1: Soluble CHO cell lysate. Lane 2: Pure IgG stock. Lane 3: Pure Z-ELP-E2 nanoparticle. Lane 4: Initial mix. Lane 5: Precipitation 1 supernatant with 0.5 M ammonium sulfate. Lane 6: Precipitation 1 pellet resuspended in elution buffer pH 3.7. Lane 7: Precipitation 2 supernatant with 0.5M ammonium sulfate. Lane 8: Precipitation 2 pellet resuspended in PBS. Lane 9: Molecular weight marker.

The preceding affinity precipitation characterization was performed with a purified model antibody without any contaminating impurities. To evaluate the process using a more representative "mock" mAb culture, non-secreting CHO cells were harvested, concentrated, and lysed by sonication. This CHO cell lysate was mixed with the purified polyclonal antibody in media to serve as a challenging cell culture feed with a complex mixture of impurity proteins. The nanoparticle affinity precipitation process was characterized by SDS-PAGE analysis (FIG. 12). The IgG bound to the Z-domain and was selectively precipitated (lane 6) while the CHO cell lysate impurities remain in the supernatant (lane 5). Upon resolublilizing the IgG-Z-ELP-E2 complex in low pH buffer, the IgG was dissociated from the Z-domain. After another precipitation, the eluted, purified IgG was separated in the supernatant (lane 7) from the nanoparticle in the pellet (lane 8). Pictures of each step in the process are shown in FIG. 14. The eluted IgG was highly pure (>99%) and the recovery was >95%. Similar high purity and recovery were obtained using E. coli lysate as the feed stock. This mock purification demonstrates a highly efficient method of selectively capturing and purifying antibodies from a complicated mixture of media and host cell impurities.

III. CONCLUSION

The monoclonal antibody market is rapidly expanding and the increased demand has presented a challenge to the current platform production process. Protein A chromatography has been identified as a potential bottleneck, sparking interest in evaluating alternative non-chromatographic capture technologies. Affinity precipitation with Z-ELP biopolymers is a promising alternative because of its high antibody selectivity and operational benefits. However, elevated temperature and salt concentrations necessary for precipitation may impact product quality and purification capacity. Therefore, it is ideal to eliminate the need for a heating step while minimizing the required salt to precipitate ELP. To accomplish this, we enlarged the scale of ELP aggregate formation through the bio-conjugation of Z-ELP to a self-assembled E2 scaffold using SrtA A ligation.

After demonstrating the Z-ELP-E2 ligation product consisted of monodisperse nanoparticles with the expected size and structure, the $T_t$, IgG purification yield, and IgG bound aggregate size was compared for ligated and free Z-ELP. The nanoparticles exhibited significantly lower $T_t$s and smaller temperature transition ranges. In PBS, there was a >10° C. difference in $T_t$s between ligated and free Z-ELP. The nanoparticle affinity precipitation of a human polyclonal IgG resulted in a recovery and purity of >95% using 0.5 M ammonium sulfate at room temperature. Nanoparticle IgG recovery was significantly higher than free Z-ELP under the same solution conditions because of the lower $T_t$.

The binding of IgG to the nanoparticle resulted in the polymerization of large aggregate particles>1 μm at room temperature without the addition of any salt and the nanoparticle precipitate size was determined to be an order of magnitude larger than free Z-ELP. Lastly, the affinity precipitation process was challenged with a mock mAb culture and high yield and purity was obtained. In conclusion, a new framework for designing enhanced nanoparticle capturing scaffolds was established by improving aggregation through increased scaffold dimension and target protein-triggered crosslinking. The ability to induce isothermal switching of phase separation by target protein binding significantly minimizes the requirement of salt and eliminates the requirement of a heating step. In addition, the multi-valent IgG-nanoparticle crosslinking yielded stable precipitates that allow for washing and extended storage in low salt buffers until elution at low pH.

All documents, books, manuals, papers, patents, published patent applications, guides, abstracts, and/or other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed:

1. A method for purifying a target protein produced by host cells without chromatography, comprising
   (a) separating the target protein from the host cells;
   (b) exposing the separated target protein of step (a) to a nanoparticle in a first solution to form a complex of the target protein and the nanoparticle, wherein the nanoparticle comprises a fusion protein and a scaffolding domain, wherein the fusion protein is covalently bound to the scaffolding domain, wherein the fusion protein comprises an affinity domain capable of binding specifically the target protein and a stimuli responsive precipitation domain, wherein the nanoparticle is bound specifically to the target protein in the first solution, wherein the scaffolding domain comprises self-assembled proteins and has a diameter of at least 10 nm, wherein the stimuli responsive precipitation domain is an elastin-like polypeptide (ELP) and the scaffolding domain is an E2 core of the pyruvate dehydrogenase complex (E2), wherein the first solution has a salt concentration of 50-200 mM and a pH of 6-9, whereby the complex precipitates out of the first solution;
   (c) adding the precipitated complex of step (b) to a second solution having a pH less than 4, whereby the precipitated complex of step (b) is solubilized and the target protein is released from the nanoparticles in the second solution; and
   (d) applying a stimulus to the second solution of step (c), wherein the stimulus comprises increasing the salt concentration of the second solution, whereby the solubilized nanoparticle of step (c) precipitates out of the second solution and the released target protein of step (c) is purified from the host cells.

2. The method of claim 1, wherein the first solution has a temperature of 15-25° C., and wherein the molar ratio of the affinity domain to the target protein in the first solution is in the range of 3:1-6:1.

3. The method of claim 1, further comprising changing the first solution.

4. The method of claim 1, further comprising changing temperature of the first solution, salt concentration of the first solution, pH of the first solution or a combination thereof.

5. The method of claim 1, wherein the first solution has a temperature of 15-25° C., and wherein the method excludes changing the temperature of the first solution.

6. The method of claim 1, wherein the first solution has a temperature of 15-25° C., further comprising changing the temperature of the first solution of no more than 10° C.

7. The method of claim 1, wherein the method excludes changing the salt concentration of the first solution.

8. The method of claim 1, wherein the salt has a cation selected from the group consisting of ammonium, potassium and sodium.

9. The method of claim 1, wherein the salt has an anion selected from the group consisting of phosphate, sulfate, carboxylate and chloride.

10. The method of claim 1, wherein the method excludes changing the pH of the first solution.

11. The method of claim 1, further comprising changing the pH of the first solution by no more than 5 pH units.

12. The method of claim 1, wherein the stimulus further comprises a change of pH of the second solution.

13. The method of claim 1, wherein the stimulus further comprises changing the temperature of the second solution to less than 25° C.

14. The method of claim 1, wherein the target protein is an antibody selected from the group consisting of immunoglobulin (Ig) types IgG, IgD, IgE, IgA and IgM.

15. The method of claim 1, wherein the host cells are selected from the group consisting of Chinese hamster ovary (CHO) cells, *Escherichia coli* cells, *Saccharomyces cerevisiae* cells, *Pichia pastoris* cells, and Human embryonic kidney (HEK) cells.

16. The method of claim 1, wherein the affinity domain is selected from the group consisting of Z-domain, protein A, protein G, protein L, protein M, single-chain variable fragment (scFv) domain, and a combination thereof.

17. The method of claim 1, wherein the affinity domain is Z-domain.

\* \* \* \* \*

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: X
<222> LOCATION: (4)..(4)
<223> OTHER INFORMATION: X is any amino acid except proline

<400> SEQUENCE: 1

Val Pro Gly Xaa Gly
1               5
```